United States Patent
Tanaka

(10) Patent No.: US 12,171,559 B2
(45) Date of Patent: Dec. 24, 2024

(54) ADJUSTMENT DEVICE, ADJUSTMENT SYSTEM, AND ADJUSTMENT METHOD

(71) Applicant: Mitsubishi Electric Corporation, Tokyo (JP)

(72) Inventor: Kento Tanaka, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 18/037,936

(22) PCT Filed: Feb. 3, 2021

(86) PCT No.: PCT/JP2021/003813
§ 371 (c)(1),
(2) Date: May 19, 2023

(87) PCT Pub. No.: WO2022/168187
PCT Pub. Date: Aug. 11, 2022

(65) Prior Publication Data
US 2023/0404456 A1    Dec. 21, 2023

(51) Int. Cl.
*A61B 5/18* (2006.01)
*B60K 28/06* (2006.01)
(Continued)

(52) U.S. Cl.
CPC .............. *A61B 5/18* (2013.01); *B60K 28/06* (2013.01); *B60W 40/08* (2013.01); *G08B 21/06* (2013.01); *G08G 1/16* (2013.01)

(58) Field of Classification Search
CPC ......... A61B 5/18; B60K 28/06; B60W 40/08; B60W 50/14; B60W 2540/21;
(Continued)

(56) References Cited

U.S. PATENT DOCUMENTS 5,821,860 A * 10/1998 Yokoyama ........... B60K 28/066
340/576
2010/0241021 A1   9/2010 Morikawa et al.
(Continued)

FOREIGN PATENT DOCUMENTS

JP    2007-269268 A    10/2007
JP    2012-245091 A    12/2012
(Continued)

OTHER PUBLICATIONS

International Search Report (PCT/ISA/210) issued in PCT/JP2021/003813, dated Apr. 27, 2021.

*Primary Examiner* — Ryan W Sherwin
(74) *Attorney, Agent, or Firm* — Birch, Stewart, Kolasch & Birch, LLP

(57) ABSTRACT

An adjustment device is configured to collect estimation results of the estimated state of the occupant; determine whether or not it is necessary to check the state of the occupant on the basis of the estimation results; determine a behavior of the occupant on the basis of behavior determination information and set the state of the occupant when it is determined that it is necessary to check the state of the occupant; and output adjustment information for causing an occupant state estimating device to adjust a state estimation condition used for estimating the state of the occupant so that the estimation result of the state of the occupant becomes the set state of the occupant.

4 Claims, 12 Drawing Sheets

(51) Int. Cl.
    *B60W 40/08*     (2012.01)
    *G08B 21/06*     (2006.01)
    *G08G 1/16*     (2006.01)

(58) Field of Classification Search
    CPC ....... B60W 2540/22; B60W 2540/221; B60W 2540/223; G08B 21/06; G08G 1/16; G08G 1/167; G08G 1/096791; G06N 3/08; G06V 20/597
    See application file for complete search history.

(56) References Cited

U.S. PATENT DOCUMENTS

| | | | | |
|---|---|---|---|---|
| 2011/0224875 | A1* | 9/2011 | Cuddihy | B60W 10/18 701/1 |
| 2014/0062704 | A1 | 3/2014 | Kubotani et al. | |
| 2014/0309813 | A1* | 10/2014 | Ricci | G06V 20/59 701/1 |
| 2015/0286191 | A1* | 10/2015 | El Dokor | G05B 13/0265 700/47 |
| 2016/0187992 | A1* | 6/2016 | Yamamoto | G06F 3/017 345/156 |
| 2017/0261984 | A1* | 9/2017 | Ichikawa | B60W 50/14 |
| 2018/0055438 | A1* | 3/2018 | Nakahata | A61B 5/1128 |
| 2018/0174457 | A1* | 6/2018 | Taylor | G06N 3/045 |
| 2018/0251122 | A1* | 9/2018 | Golston | B60W 40/08 |
| 2019/0225232 | A1* | 7/2019 | Blau | G05D 1/0088 |
| 2020/0023856 | A1* | 1/2020 | Kim | G10L 17/00 |
| 2020/0207358 | A1* | 7/2020 | Katz | G02B 27/0093 |
| 2020/0287497 | A1* | 9/2020 | Nagata | G06N 3/08 |
| 2020/0307644 | A1* | 10/2020 | Hattori | B60W 60/0053 |
| 2021/0114619 | A1* | 4/2021 | Mimura | B62D 6/00 |
| 2021/0269045 | A1* | 9/2021 | Katz | G02B 27/0093 |
| 2021/0316737 | A1* | 10/2021 | Iwase | A61B 5/4035 |
| 2022/0153302 | A1* | 5/2022 | Arechiga-Gonzalez | B60W 50/14 |
| 2022/0315031 | A1* | 10/2022 | Nakamura | G06V 20/597 |
| 2023/0347903 | A1* | 11/2023 | Katz | G06V 20/597 |

FOREIGN PATENT DOCUMENTS

| | | |
|---|---|---|
| JP | 2016-45714 A | 4/2016 |
| JP | 2019-131096 A | 8/2019 |
| JP | 2020-154976 A | 9/2020 |
| WO | WO 2010/032491 A1 | 3/2010 |

\* cited by examiner

ADJUSTMENT DEVICE, ADJUSTMENT SYSTEM, AND ADJUSTMENT METHOD

TECHNICAL FIELD

The present disclosure relates to an adjustment device, an adjustment system, and an adjustment method for adjusting an occupant state estimation method in an occupant state estimating device that estimates an occupant state.

BACKGROUND ART

Conventionally, an occupant state estimating device that estimates whether an occupant state is a normal state or an abnormal state during traveling of a vehicle is known. There are various estimation methods for estimating the occupant state used in the occupant state c estimating device.

Whether the occupant state is a normal state or an abnormal state differs depending on personal characteristics of the occupant. Therefore, among various estimation methods for estimating the occupant state, there may be, for example, a method in which a certain occupant is easily estimated to be in an abnormal state and a method in which the occupant is hardly estimated to be in an abnormal state when the certain occupant is to be estimated. As a result, depending on the estimation method, the abnormal state may be overdetected or undetected.

On the other hand, for example, a technique of confirming to an occupant as to an estimated occupant state whether or not the occupant is actually in the estimated state is known.

For example, Patent Literature 1 discloses a technique of determining a driver's driving incapability state by any of frame-out determination, unsafe posture determination, unsafe direction determination, shake determination, and white-eye determination, and confirming to the driver whether or not the driver is in the driving incapability state when determining that the driver is in the driving incapability state.

CITATION LIST

Patent Literature

Patent Literature 1: JP 2016-45714 A

SUMMARY OF INVENTION

Technical Problem

The conventional technique as disclosed in Patent Literature 1 has a problem that, even if the driver is once confirmed whether or not the driver is in the driving incapability state when the driver is determined to be in the driving incapability state, the confirmation result is not used for the subsequent determination that the driver is in the driving incapability state. As a result, in the conventional technique, for example, when the driver's driving incapability state has not been appropriately determined, there is a possibility that the inappropriate determination is repeated.

The present disclosure has been made to solve the above problem, and an object of the present disclosure is to provide an adjustment device capable of adjusting a method of estimating an occupant state in an occupant state estimating device that estimates an occupant state.

Solution to Problem

An adjustment device according to the present disclosure is an adjustment device that adjusts an estimation method of a state of an occupant in at least one occupant state estimating device that includes a plurality of occupant state estimating devices and estimates the state of the occupant, the adjustment device including: processing circuitry configured to collect estimation results of the state of the occupant estimated by the plurality of occupant state estimating devices; determine whether or not it is necessary to check the state of the occupant on a basis of the collected estimation results and a machine learning model that outputs checking necessity information indicating whether or not it is necessary to check the state of the occupant using the estimation results as an input; determine a behavior of the occupant on a basis of behavior determination information for determining the behavior of the occupant and set the state of the occupant when the processing circuitry determines that it is necessary to check the state of the occupant; output adjustment information for causing the at least one occupant state estimating device to adjust a state estimation condition used for estimating the state of the occupant in such a manner that the state of the occupant is estimated as the state of the occupant having been set; collect, as reference information, at least one of vehicle interior environment determination information for determining an environment in a vehicle and abnormal-time motion determination information for determining a motion that the occupant tends to make in a case where the occupant is in an abnormal state; and determine whether or not it is necessary to check the state of the occupant on a basis of the collected estimation results, the collected reference information, and the machine learning model that uses the estimation results and the reference information as inputs and outputs the checking necessity information.

Advantageous Effects of Invention

According to the present disclosure, it is possible to adjust a method of estimating an occupant state in an occupant state estimating device that estimates an occupant state.

BRIEF DESCRIPTION OF DRAWINGS

FIG. 4 is a flowchart for explaining a specific operation of step ST3 in FIG. 2.

DESCRIPTION OF EMBODIMENTS

Figure 1:
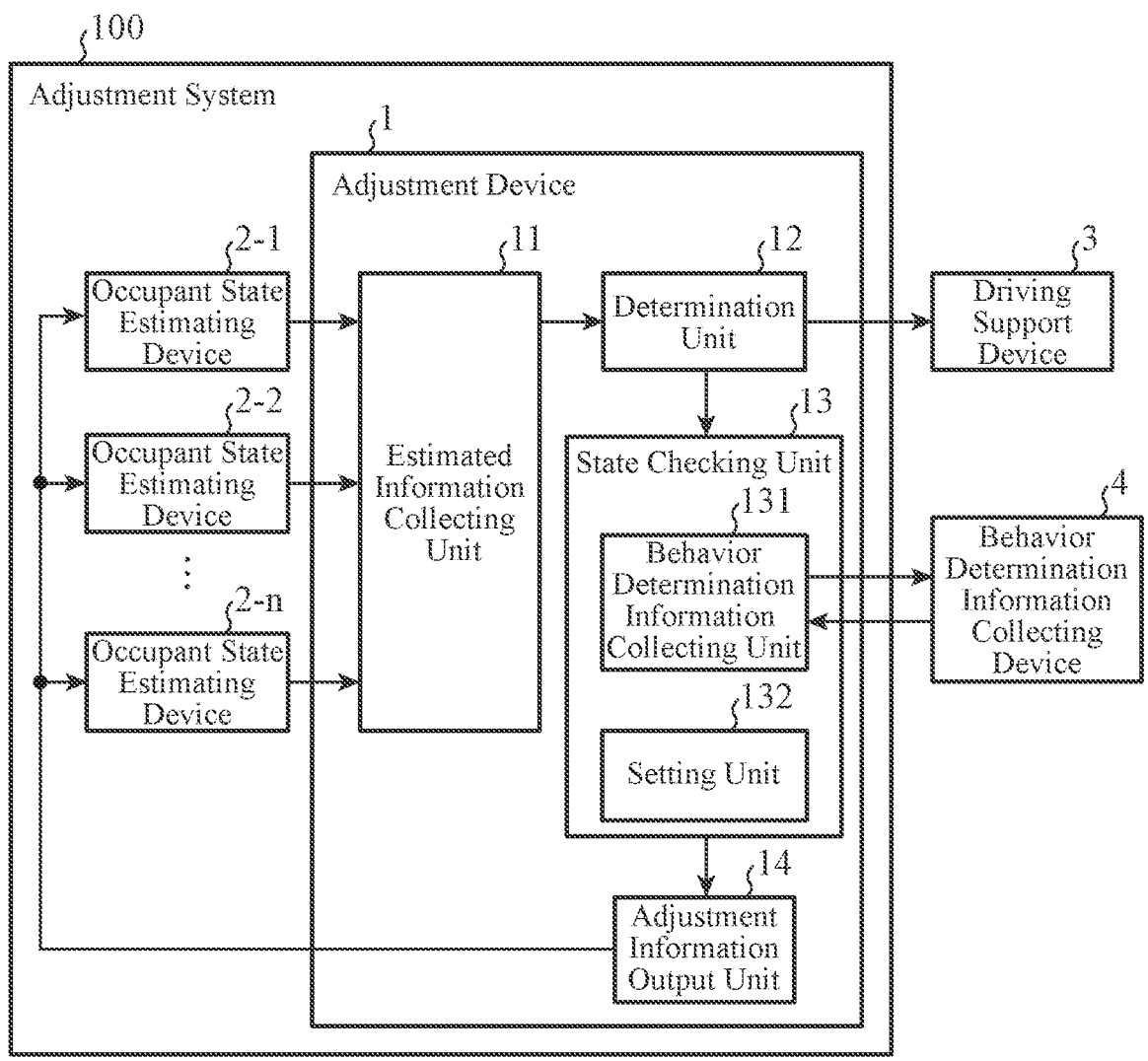
FIG. 1 is a diagram illustrating a configuration example of an adjustment device according to a first embodiment.

Hereinafter, embodiments of the present disclosure will be described in detail with reference to the drawings.

First Embodiment

An adjustment device according to a first embodiment is mounted on a vehicle. The adjustment device is connected to a plurality of occupant state estimating devices, and the adjustment device and the plurality of occupant state estimating devices constitute an adjustment system. The plurality of occupant state estimating devices are also mounted on the vehicle.

The occupant state estimating device estimates a state of an occupant present in the vehicle interior. Specifically, the occupant state estimating device estimates whether an occupant state is in a "normal state" or in an "abnormal state" by using information regarding the occupant of the vehicle (hereinafter referred to as "occupant-related information".). In the first embodiment, the occupant of the vehicle is assumed to be a driver, and the occupant state estimating device estimates, for example, whether the driver is in a "normal state" that can appropriately drive or in an "abnormal state" that interferes with driving. More specifically, the "normal state" refers to, for example, a state in which the occupant can concentrate on driving, a state in which the occupant is awake, a state in which the occupant is not exhausted, or a state in which the occupant is not irritated. The "abnormal state" is a state in which the occupant is not in the "normal state" as described above.

The occupant-related information is, for example, biological information of the occupant, a captured image obtained by imaging the occupant (hereinafter referred to as an "in-vehicle captured image"), speech sound of the occupant, or information regarding operation of the vehicle by the occupant (hereinafter referred to as "vehicle operation information"). In the first embodiment, it is assumed that information regarding a state of the vehicle changed by an operation of the vehicle by the occupant (hereinafter referred to as "vehicle state information") and information around the vehicle in which the occupant is present (hereinafter referred to as "vehicle peripheral information") are also included in the occupant-related information.

The biological information of the occupant includes, for example, information regarding a body temperature, a perspiration degree, or a heartbeat of the occupant.

The vehicle operation information includes, for example, information regarding a steering wheel operation amount, an accelerator operation amount, a brake operation amount, the presence or absence of a button operation, or the presence or absence of a blinker operation.

The vehicle state information includes, for example, a vehicle speed, an acceleration of the vehicle, or position information of the vehicle.

The vehicle peripheral information includes, for example, a captured image (hereinafter referred to as "vehicle exterior captured image") obtained by imaging the periphery of the vehicle, distance information with respect to an object outside the vehicle, or information regarding another vehicle present around the vehicle.

For example, the occupant state estimating device acquires biological information of the occupant from a biological sensor mounted in the vehicle, and estimates whether the occupant is in a normal state or an abnormal state by comparing the biological information of the occupant with a preset condition (hereinafter referred to as a "state estimation condition".) for estimating the occupant state.

Furthermore, for example, the occupant state estimating device acquires an in-vehicle captured image from a camera (hereinafter referred to as an "in-vehicle camera".) that captures an image of the inside of the vehicle, and recognizes the facial expression, the emotion, the line of sight, the degree of eye opening, the size of the pupil, the direction of the face, or the posture of the body of the occupant using a known image recognition technology. Note that the in-vehicle camera may be shared with, for example, a so-called "Driver Monitoring System, DMS"". Then, the occupant state estimating device estimates whether the occupant is in the normal state or the abnormal state by comparing the face expression, the emotion, the line of sight, the degree of eye opening, the size of the pupil, the direction of the face, or the posture of the body of the occupant with the state estimation condition.

Furthermore, for example, the occupant state estimating device collects speech sound of the occupant from a microphone that collects sound in the vehicle, and recognizes speech of the occupant using a known sound recognition technology. Then, the occupant state estimating device estimates whether the occupant is in the normal state or the abnormal state by comparing the recognized speech with the state estimation condition.

Further, for example, the occupant state estimating device acquires the vehicle operation information from various sensors such as a steering angle sensor or a brake sensor mounted on the vehicle. Then, the occupant state estimating device estimates whether the occupant is in the normal state or the abnormal state by comparing the vehicle operation information with the state estimation condition.

Further, for example, the occupant state estimating device acquires vehicle state information from a sensor mounted on the vehicle such as a vehicle speed sensor or an acceleration sensor, or a global positioning system (GPS). Then, the occupant state estimating device estimates whether the occupant is in the normal state or the abnormal state by comparing the vehicle state information with the state estimation condition.

In addition, for example, the occupant state estimating device acquires vehicle peripheral information by a camera (hereinafter, referred to as an "exterior imaging camera")

that images the periphery of the vehicle, a distance sensor or a LiDAR which are mounted on the vehicle, or from another vehicle by vehicle-to-vehicle communication, or by communication with a so-called infrastructure installed outside the vehicle. Then, the occupant state estimating device estimates whether the occupant is in the normal state or the abnormal state by comparing the inter-vehicle distance with the preceding vehicle or the positional relationship between the white line and the vehicle determined for the vehicle peripheral information using a known image recognition technology or the like with the state estimation condition. Note that the positional relationship between the white line and the vehicle is, for example, a positional relationship indicating where the vehicle is traveling with respect to the lane.

For example, a threshold value is set in the state estimation condition.

For example, the occupant state estimating device estimates the state of the occupant by comparing the body temperature of the occupant with a threshold set in the state estimation condition. For example, the occupant state estimating device estimates an abnormal state when the body temperature of the occupant is equal to or greater than a threshold, and estimates a normal state when the body temperature of the occupant is less than the threshold.

Further, for example, the occupant state estimating device estimates the state of the occupant by comparing the eye opening degree of the occupant with a threshold set in the state estimation condition. For example, the occupant state estimating device estimates an abnormal state when the eye opening degree of the occupant is less than the threshold, and estimates a normal state when the eye opening degree of the occupant is equal to or greater than the threshold.

For example, some conditions may be set as the state estimation condition. For example, a condition for estimating an abnormal state in a case where the feeling of anger of the occupant is recognized may be set as the state estimation condition. In this case, for example, the occupant state estimating device estimates an abnormal state when recognizing the feeling of anger of the occupant on the basis of the vehicle interior captured image, and estimates a normal state when not recognizing the feeling of anger of the occupant.

The occupant state estimating device may estimate the state of the occupant by combining a plurality of types of occupant-related information such as biological information and an in-vehicle captured image.

Each of the plurality of occupant state estimating devices estimates the state of the occupant by the above-described method.

The adjustment device collects an estimation result of the state of the occupant from the plurality of occupant state estimating devices. Specifically, the estimation result of the occupant is information indicating whether the occupant is in a normal state or an abnormal state. Then, the adjustment device adjusts the method of estimating the state of the occupant in the occupant state estimating device on the basis of the estimation result of the state of the occupant by the occupant state estimating device. Specifically, the adjustment device checks the current state of the occupant as necessary for the estimation result by the occupant state estimating device. Upon checking the state of the occupant, the adjustment device outputs information (hereinafter referred to as "adjustment information") for causing the occupant state estimating device to adjust the state estimation condition so that the state of the occupant is estimated to be the state of the occupant checked by the adjustment device in the method for estimating the state of the occupant estimated as the estimation result collected by the occupant state estimating device. When acquiring the adjustment information from the adjustment device, the occupant state estimating device adjusts the state estimation condition on the basis of the adjustment information.

As described above, the occupant state estimating device estimates the state of the occupant by various methods. Here, when the state of the occupant is the normal state or the abnormal state differs depending on personal characteristics or the like of the occupant. As a specific example, for example, when a certain occupant feels drowsy, that is, when the occupant is in an abnormal state, the occupant can cause the vehicle to travel almost straight, but tends to close eyes. In this case, for example, there is a possibility that the occupant state estimating device estimates an abnormal state when estimating the state of the occupant on the basis of the eye opening degree of the occupant, and does not estimate an abnormal state when estimating the state of the occupant on the basis of the steering wheel operation amount.

On the other hand, for example, it is assumed that when another occupant feels drowsy, the occupant tends not to be able to cause the vehicle to travel straight although the occupant can open his/her eyes to some extent. In this case, for example, the occupant state estimating device may estimate that the state of the occupant is the abnormal state when estimating the state of the occupant on the basis of the steering wheel operation amount, and may not estimate that the state of the occupant is the abnormal state when estimating the state of the occupant on the basis of the eye opening degree.

As described above, since a certain occupant and another occupant are different in appearance of drowsiness, when the occupant state estimating device estimates the state of the occupant using the state determination condition uniformly set for the occupant-related information, there is a problem that, for example, a state in which the occupant feels drowsy, in other words, overdetection or undetection of an abnormal state is caused.

Thus, the adjustment device checks the current state of the occupant as necessary. Then, the adjustment device causes the occupant state estimating device to adjust the method for estimating the state of the occupant in the occupant state estimating device. As a result, the adjustment device performs adjustment so that the occupant state estimating device estimates the state of the occupant according to the personal characteristics or the like of the occupant. Details of the adjustment of the method for estimating the state of the occupant in the occupant state estimating device performed by the adjustment device will be described later.

Note that the occupant state estimating device outputs the estimation result of the state of the occupant not only to the adjustment device but also to a driving support device that performs driving control of the vehicle. The driving support device outputs an alarm, controls the vehicle, or the like on the basis of the estimation result of the state of the occupant output from the occupant state estimating device.

FIG. 1 is a diagram illustrating a configuration example of an adjustment device 1 according to the first embodiment.

As illustrated in FIG. 1, an adjustment system 100 includes the adjustment device 1 and a plurality of occupant state estimating devices (2-1 to 2-n).

In FIG. 1, the plurality of occupant state estimating devices (2-1 to 2-n) are separate devices, but the plurality of occupant state estimating devices (2-1 to 2-n) may be provided in one device. In the following first embodiment, the plurality of occupant state estimating devices (2-1 to 2-*n*) are also collectively referred to as an occupant state estimating device 2.

The adjustment device 1 includes an estimated information collecting unit 11, a determination unit 12, a state checking unit 13, and an adjustment information output unit 14. The state checking unit 13 includes a behavior determination information collecting unit 131 and a setting unit 132.

The estimated information collecting unit 11 collects estimation results of the state of the occupant estimated by the occupant state estimating devices 2. Note that it is assumed that the estimation result of the state of the occupant output from the occupant state estimating device 2 is assigned with information that can identify the occupant state estimating device 2 that has estimated the estimation result. A time (hereinafter, referred to as "estimated time") at which the state of the occupant is estimated may be further assigned to the estimation result.

The estimated information collecting unit 11 outputs a plurality of collected estimation results to the determination unit 12.

At this time, the estimated information collecting unit 11 stores the plurality of collected estimation results in a storage unit (not illustrated) in association with the time when the estimation results are collected. For example, in a case where the estimated time is not assigned to the estimation result, the estimated information collecting unit 11 assigns the time when the estimation result is collected as the estimated time. The estimated information collecting unit 11 causes the storage unit to store the estimation result for a preset period (hereinafter, referred to as an "estimation result accumulation period").

The determination unit 12 determines whether or not it is necessary to check the state of the occupant on the basis of a plurality of estimation results collected by the estimated information collecting unit 11. In the first embodiment, the determination made by the determination unit 12 as to whether or not it is necessary to check the state of the occupant is also referred to as "determination processing".

Specifically, when any one of the plurality of estimation results collected by the estimated information collecting unit 11 indicates an abnormal state and there is an estimation result indicating a normal state among other estimation results, the determination unit 12 determines that it is necessary to check the state of the occupant. More specifically, in a case where at least one of the plurality of estimation results collected by the estimated information collecting unit 11 indicates an abnormal state, when there is an estimation result indicating a normal state in other estimation results, and there is an estimation result indicating an abnormal state continuously for a preset period (hereinafter referred to as a "determination period") among the estimation results indicating an abnormal state, the determination unit 12 determines that it is necessary to check the state of the occupant.

The determination unit 12 can determine whether or not an abnormal state is indicated continuously for a determination period from the estimation result stored in the storage unit. Note that in the first embodiment, the estimation result accumulation period is longer than the determination period. For example, the determination period may be a fixed value or a variable value. For example, the determination unit 12 may change the length of the determination period by the occupant. For example, a determination period is set when the occupant gets in the vehicle, and the determination unit 12 performs the determination processing using the determination period set by the occupant.

When there is no estimation result indicating an abnormal state continuously for the determination period among the estimation results indicating an abnormal state, the determination unit 12 determines that it is not necessary to check the state of the occupant. It is conceivable that the fact that the abnormal state is not continuously indicated during the determination period means that, for example, the abnormal state estimated by the occupant state estimating device 2 has been a temporary abnormal state, or the state of the occupant has returned from the abnormal state to the normal state during the determination period.

In addition, when all of the plurality of estimation results collected by the estimated information collecting unit 11 indicate an abnormal state and when all of the plurality of estimation results collected by the estimated information collecting unit 11 indicate a normal state, the determination unit 12 determines that it is not necessary to check the state of the occupant.

When determining that it is necessary to check the state of the occupant, the determination unit 12 outputs information (hereinafter, referred to as "state checking instruction information") for causing the state checking unit 13 to check the state of the occupant. The determination unit 12 outputs the estimation result of the state of the occupant by the occupant state estimating device 2 together with the state checking instruction information.

In addition, in the first embodiment, the determination unit 12 generates information (hereinafter referred to as "comprehensive result information") indicating a plurality of estimation results collected by the estimated information collecting unit 11, and outputs the generated comprehensive result information to the driving support device 3. The comprehensive result information is, for example, information indicating a ratio of the occupant state estimating devices 2 that estimated as an abnormal state among the occupant state estimating devices 2.

The driving support device 3 is mounted on the vehicle. When acquiring the comprehensive result information output from the determination unit 12, the driving support device 3 can check whether or not there is a space where emergency evacuation can be applied ahead, before the occupant becomes completely abnormal and the vehicle needs to be stopped on the basis of the comprehensive result information.

Note that the driving support device 3 performs driving support on the basis of the estimation result of the state of the occupant estimated by the occupant state estimating device 2. Specifically, for example, in a case where a predetermined number or more of estimation results among all the estimation results indicate an abnormal state on the basis of the estimation result of the state of the occupant, the driving support device 3 outputs an alarm to the occupant. Further, for example, when all the estimation results indicate an abnormal state, the driving support device 3 causes the vehicle to make an emergency stop. Note that in FIG. 1, an arrow indicating that an estimation result is output from the occupant state estimating device 2 to the driving support device 3 is not illustrated.

In the first embodiment, as described above, the determination unit 12 has a function of outputting the comprehensive result information to the driving support device 3, but this is merely an example. It is not essential for the determination unit 12 to have a function of outputting the comprehensive result information to the driving support device 3.

When the determination unit 12 determines that it is necessary to check the state of the occupant, in other words, when the state checking instruction information is output from the determination unit 12, the state checking unit 13 checks the current state of the occupant. Specifically, the state checking unit 13 determines the behavior of the occupant on the basis of information for determining the behavior of the occupant (hereinafter, referred to as "behavior determination information"), and sets the state of the occupant. In the first embodiment, the setting of the state of the occupant based on the behavior determination information performed by the state checking unit 13 is also referred to as "occupant state checking processing".

The "occupant state checking processing" performed by the state checking unit 13 will be described in detail.

First, the behavior determination information collecting unit 131 of the state checking unit 13 collects behavior information from a behavior determination information collecting device 4.

The behavior determination information collecting device 4 is, for example, a vehicle interior imaging camera, a microphone mounted on the vehicle, or a car navigation device mounted on the vehicle, and the behavior determination information is, for example, a vehicle interior captured image captured by the vehicle interior imaging camera, speech sound collected by the microphone, or operation information of a device such as a button provided in the car navigation device.

Note that the specific example of the behavior determination information collecting device 4 described above is merely an example. The behavior determination information collecting device 4 includes various devices that collect information capable of determining the behavior of the occupant.

The behavior determination information collecting unit 131 may collect the behavior determination information of the occupant by requesting a response from the occupant, or may collect the behavior determination information of the occupant without requesting a response from the occupant.

For example, when collecting the behavior determination information of the occupant by requesting a response from the occupant, the behavior determination information collecting unit 131 outputs information (hereinafter, referred to as "inquiry information") for making an inquiry to the occupant to a device such as the behavior determination information collecting device 4, and collects the behavior determination information. Specifically, for example, the behavior determination information collecting unit 131 outputs inquiry information for causing a car navigation device to output a voice "How are you?" from a speaker included in the car navigation device. After the output of the inquiry information, the behavior determination information collecting unit 131 collects, as the behavior determination information, speech sound of the occupant responding to the inquiry from the car navigation device. Furthermore, for example, the behavior determination information collecting unit 131 outputs inquiry information for causing the car navigation device to display a message "Please press an OK button if there is no problem with your physical condition" and the OK button on a display unit included in the car navigation device. After outputting the inquiry information, the behavior determination information collecting unit 131 collects, as the behavior determination information, the operation information of the OK button in response to the inquiry from the car navigation device.

On the other hand, in a case where the behavior determination information collecting unit 131 collects the behavior determination information of the occupant without requesting a response from the occupant, the behavior determination information collecting unit collects, as the behavior determination information, a vehicle interior captured image, speech sound, or the like constantly output from the behavior determination information collecting device 4.

When the behavior determination information collecting unit 131 collects the behavior determination information, next, the setting unit 132 of the state checking unit 13 determines the behavior of the occupant on the basis of the behavior determination information collected by the behavior determination information collecting unit 131, and sets whether the state of the occupant is the normal state or the abnormal state on the basis of the determined behavior.

A method by which the setting unit 132 sets the state of the occupant will be described with a specific example.

First, the setting unit 132 determines the behavior of the occupant on the basis of the behavior determination information collected by the behavior determination information collecting unit 131. In the first embodiment, the behavior of the occupant includes, for example, the movement of the face of the occupant and the motion of the occupant. The movement of the face of the occupant includes, for example, a facial expression, nodding, a direction of a line of sight, an eye opening degree, or a direction of the face. The motion of the occupant is, for example, a motion for responding to an inquiry from a device such as the behavior determination information collecting device 4, speech, or maintaining awakening. The response to the inquiry from the device includes, for example, a response by speech or a response by operating a device mounted on the vehicle. The speech includes, for example, a speech to a device such as a car navigation device, a conversation with a passenger, a soliloquy, or a murmur. The motion for maintaining awakening is, for example, a motion in which the occupant pinches his/her body or a motion in which the occupant taps his/her cheek.

The setting unit 132 determines the behavior of the occupant as described above using a known technique on the basis of the behavior determination information. Specifically, for example, the setting unit 132 determines the behavior of the occupant using a known image recognition technology for the vehicle interior captured image. Furthermore, for example, the setting unit 132 determines the behavior of the occupant using a known speech recognition technology for the speech sound. Furthermore, for example, the setting unit 132 determines the behavior of the occupant on the basis of the operation information of the button from the car navigation device. For example, the setting unit 132 may determine the behavior of the occupant by combining the operation information of the button and the vehicle interior captured image.

When determining the behavior of the occupant, the setting unit 132 sets the state of the occupant on the basis of the determined behavior of the occupant. The state of the occupant set by the setting unit 132 is a normal state or an abnormal state.

The setting unit 132 sets the state of the occupant on the basis of, for example, the determined behavior of the occupant and a preset condition under which the occupant is recognized to be in a normal state (hereinafter referred to as "normal condition"). When the behavior of the occupant satisfies the normal condition, the setting unit 132 sets the state of the occupant to the normal state. On the other hand, when the behavior of the occupant does not satisfy the normal condition, the setting unit 132 sets the state of the occupant to the abnormal state.

As the normal condition, for example, the following conditions (1) to (6) are set.

(1) The behavior is a response corresponding to the inquiry information output by the behavior determination information collecting unit 131, in other words, a response to an inquiry output from the device.
(2) The behavior is not a response corresponding to the inquiry information output by the behavior determination information collecting unit 131 but a conversation with a passenger (The behavior is not a response to an inquiry output from the device but a response to a speech of a passenger.).
(3) The behavior is a response to an inquiry output from the device or a response to a speech of a passenger, and is a response within a preset time.
(4) The behavior is a response to an inquiry output from the device or a response to a speech of a passenger, and there is no change in voice quality.
(5) The behavior is not a preset behavior (for example, a motion of the occupant pinching his/her body, or a motion of the occupant tapping his/her cheek, talking to himself/herself, or muttering) regarded as an abnormal state.
(6) The behavior is a speech, and the speech content does not include a preset word (For example, "tired" or "sleepy") related to abnormality.

The setting unit 132 may determine whether or not the normal condition is satisfied by combining the conditions (1) to (6). For example, the setting unit 132 may combine (2) and (3) to determine that the normal condition is satisfied in a case where the determined behavior is not a response to an inquiry from the device but a response to a speech of a passenger and a conversation with the passenger is responded within a preset time. Furthermore, for example, the setting unit 132 may combine (5) and (6) to determine that the normal condition is satisfied in a case where the determined behavior is not the behavior regarded as the abnormal state and the behavior is a speech and the speech content does not include the word related to abnormality.

Note that the normal conditions (1) to (6) are merely examples. As the normal condition, an appropriate condition can be set. However, the normal condition used when the setting unit 132 sets the state of the occupant should not overlap with the state estimation condition used when the occupant state estimating device 2 estimates the state of the occupant.

The state checking unit 13 outputs the state of the occupant set by the setting unit 132 and the estimation result of the state of the occupant by the occupant state estimating device 2 output from the determination unit 12 to the adjustment information output unit 14.

As described above, the state checking unit 13 performs the "occupant state checking processing". In the following first embodiment, in the "occupant state checking processing", the state of the occupant set by the state checking unit 13 is also referred to as a "set occupant state".

The adjustment information output unit 14 outputs adjustment information for causing the occupant state estimating device 2 to adjust the state estimation condition used for estimating the state of the occupant so that the estimation result of the state of the occupant becomes the set occupant state.

Specifically, the adjustment information output unit 14 outputs adjustment information in which the estimation result of the state of the occupant estimated by each occupant state estimating device 2 is associated with the set occupant state to each occupant state estimating device 2. The estimation result of the state of the occupant estimated by each occupant state estimating device 2 is the estimation result of the state of the occupant by each occupant state estimating device 2 output from the state checking unit 13.

For example, the adjustment information output unit 14 outputs, to the occupant state estimating device 2-1, adjustment information in which the estimation result of the state of the occupant estimated by the occupant state estimating device 2-1 is associated with the set occupant state, and outputs, to the occupant state estimating device 2-2, adjustment information in which the estimation result of the state of the occupant estimated by the occupant state estimating device 2-2 is associated with the set occupant state.

Note that in the first embodiment, the adjustment information output unit 14 outputs the adjustment information to all the occupant state estimating devices 2, but this is merely an example.

For example, the adjustment information output unit 14 may output the adjustment information only to the occupant state estimating device 2 whose estimation result is different from the set occupant state. The occupant state estimating device 2 whose estimation result is different from the set occupant state can be identified on the basis of the information that can identify the occupant state estimating device 2 assigned to the estimation result.

When acquiring the adjustment information, the occupant state estimating device 2 adjusts the state estimation condition on the basis of the adjustment information. Specifically, the occupant state estimating device 2 adjusts the state estimation condition so that the state of the occupant is estimated to be the set occupant state included in the adjustment information in the method for estimating the state of the occupant estimated as the estimation result included in the adjustment information.

For example, it is assumed that the occupant state estimating device 2 estimates that the occupant is in the normal state on the basis of the eye opening degree of the occupant, but acquires the estimation result indicating the normal state and the adjustment information including the set occupant state indicating the abnormal state from the adjustment device 1. In this case, the occupant state estimating device 2 adjusts a threshold used for estimating the state of the occupant on the basis of the eye opening degree of the occupant so as to easily estimate the abnormal state.

The operation of the adjustment device 1 according to the first embodiment will be described.

Figure 2:
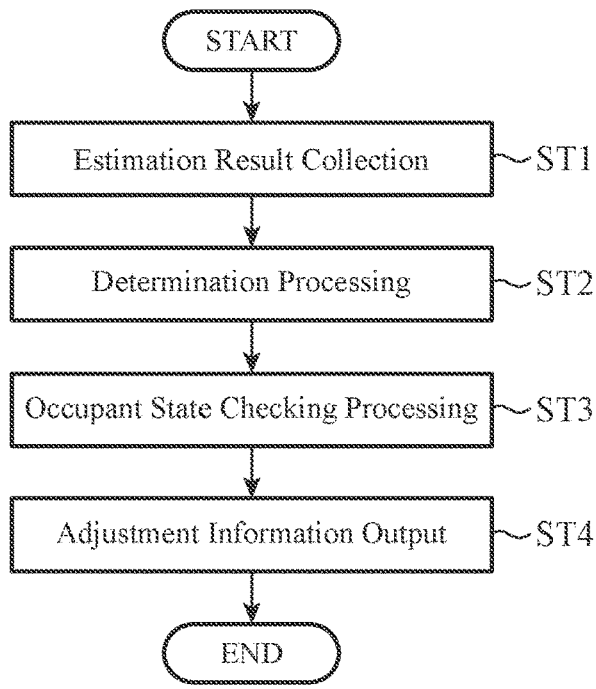
FIG. 2 is a flowchart for explaining an operation of the adjustment device according to the first embodiment.

FIG. 2 is a flowchart for explaining the operation of the adjustment device 1 according to the first embodiment. While the vehicle is traveling, the operation shown in the flowchart of FIG. 2 is repeated.

The estimated information collecting unit 11 collects estimation results of the state of the occupant estimated by the occupant state estimating devices 2 (step ST1).

The estimated information collecting unit 11 outputs the plurality of collected estimation results to the determination unit 12.

The determination unit 12 performs determination processing on the basis of the plurality of estimation results collected by the estimated information collecting unit 11 in step ST1 (step ST2).

In a case where the determination unit 12 determines that it is necessary to check the state of the occupant in step ST2, in other words, in a case where the state checking instruction information is output from the determination unit 12, the state checking unit 13 performs "occupant state checking processing" (step ST3).

When the state checking unit 13 performs the occupant state setting processing in step ST3, the adjustment information output unit 14 outputs the adjustment information to the occupant state estimating device 2 (step ST4).

Figure 3:
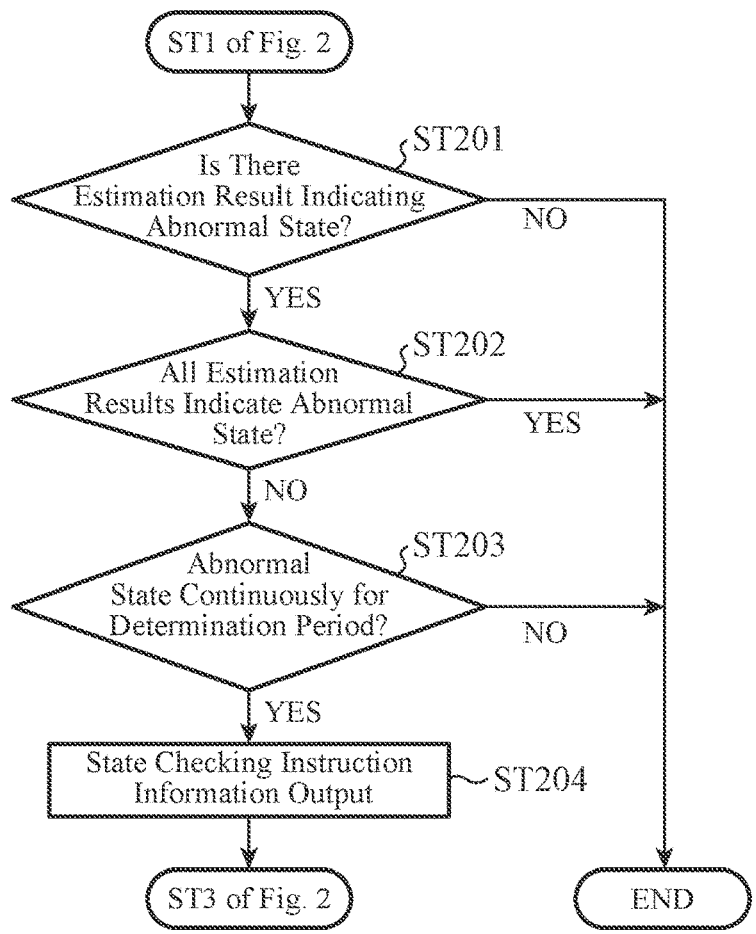
FIG. 3 is a flowchart for explaining details of determination processing of a determination unit in step ST2 of FIG. 2.

FIG. 3 is a flowchart for explaining details of the determination processing of the determination unit 12 in step ST2 of FIG. 2.

The determination unit 12 determines whether or not any one of the plurality of estimation results collected by the estimated information collecting unit 11 in step ST1 of FIG. 2 indicates an abnormal state (step ST201).

In step ST201, when the determination unit 12 determines that there is no estimation result indicating an abnormal state among the plurality of estimation results, in other words, all of the plurality of estimation results indicate a normal state ("NO" in step ST201), the adjustment device 1 ends the operation illustrated in the flowchart of FIG. 2.

In step ST201, when any one of the plurality of estimation results indicates an abnormal state ("YES" in step ST201), the determination unit 12 determines whether or not all the estimation results are estimation results indicating an abnormal state (step ST202).

In step ST202, when the determination unit 12 determines that all the estimation results indicate an abnormal state ("YES" in step ST202), the adjustment device 1 ends the operation illustrated in the flowchart of FIG. 2.

When it is determined in step ST202 that not all the estimation results are estimation results indicating an abnormal state, in other words, when there is an estimation result indicating a normal state among the other estimation results ("NO" in step ST202), the determination unit 12 determines whether or not there is an estimation result indicating an abnormal state continuously for the determination period among the estimation results indicating an abnormal state among the plurality of estimation results collected by the estimated information collecting unit 11 in step ST1 of FIG. 2 (step ST203).

In step ST203, when the determination unit 12 determines that there is no estimation result indicating an abnormal state continuously for the determination period ("NO" in step ST203), the adjustment device 1 ends the operation illustrated in the flowchart of FIG. 2.

When it is determined in step ST203 that there is an estimation result indicating an abnormal state continuously during the determination period ("YES" in step ST203), the determination unit 12 determines that it is necessary to check the state of the occupant and outputs state checking instruction information to the state checking unit 13 (step ST204).

In addition, the determination unit 12 generates comprehensive result information, and outputs the generated comprehensive result information to the driving support device 3.

Figure 4:
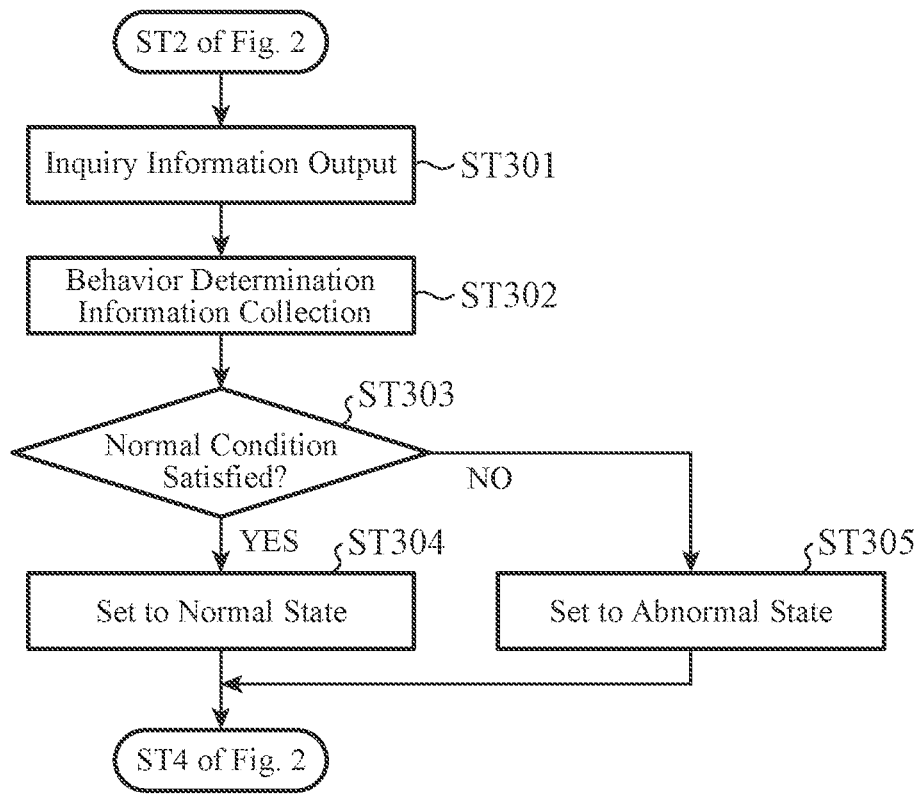
FIG. 4 is a flowchart for explaining details of "occupant state checking processing" in a case where a state checking unit sets an occupant state on the basis of behavior determination information collected by requesting a response from the occupant in the first embodiment.
Figure 5:
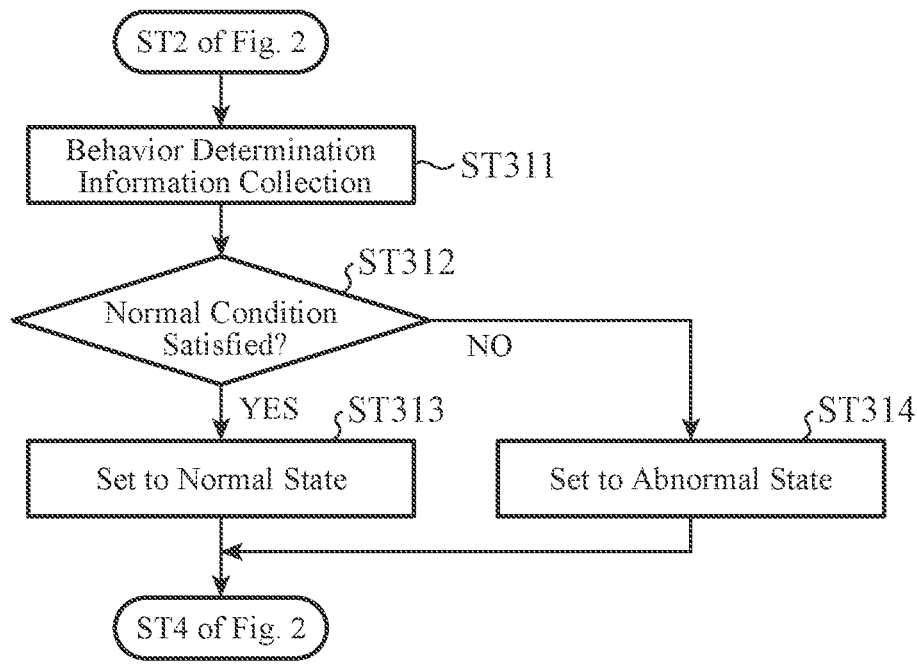
FIG. 5 is a flowchart for explaining details of "occupant state checking processing" in a case where the state checking unit sets an occupant state on the basis of behavior determination information collected without requesting a response from the occupant in the first embodiment.

FIGS. 4 and 5 are flowcharts for explaining details of the "occupant state checking processing" of the state checking unit 13 in step ST3 in FIG. 2.

FIG. 4 is a flowchart for describing details of the "occupant state checking processing" in a case where the state checking unit 13 sets the state of the occupant on the basis of the behavior determination information collected by requesting a response from the occupant. FIG. 5 is a flowchart for describing details of the "occupant state checking processing" in a case where the state checking unit 13 sets the state of the occupant on the basis of the behavior determination information collected without requesting a response from the occupant.

The state checking unit 13 performs the "occupant state checking processing" illustrated in FIG. 4 or the "occupant state checking processing" illustrated in FIG. 5.

First, the flowchart of FIG. 4 will be described.

The behavior determination information collecting unit 131 of the state checking unit 13 outputs inquiry information to the occupant to a device such as the behavior determination information collecting device 4 (step ST301), and collects the behavior determination information from the behavior determination information collecting device 4 (step ST302).

When the behavior determination information collecting unit 131 collects the behavior information in step ST302, the setting unit 132 of the state checking unit 13 determines the behavior of the occupant on the basis of the behavior determination information collected by the behavior determination information collecting unit 131. Then, the setting unit 132 determines whether or not the determined behavior of the occupant satisfies a normal condition (step ST303).

Here, the normal condition is, for example, any of the normal conditions (1) to (4) described above. For example, the setting unit 132 may determine whether or not the normal condition is satisfied by combining the normal conditions (1) to (4).

When the determined behavior of the occupant satisfies the normal condition ("YES" in step ST303), the setting unit 132 sets the state of the occupant to the normal state (step ST304).

On the other hand, when the determined behavior of the occupant does not satisfy the normal condition ("NO" in step ST303), the setting unit 132 sets the state of the occupant to the abnormal state (step ST305).

Next, the flowchart of FIG. 5 will be described.

The behavior determination information collecting unit 131 of the state checking unit 13 collects the behavior determination information from the behavior determination information collecting device 4 (step ST311).

When the behavior determination information collecting unit 131 collects the behavior determination information in step ST311, the setting unit 132 of the state checking unit 13 determines the behavior of the occupant on the basis of the behavior determination information collected by the behavior determination information collecting unit 131. Then, the setting unit 132 determines whether or not the determined behavior of the occupant satisfies a normal condition (step ST312).

Here, the normal condition is, for example, any of the normal conditions (5) to (6) described above. For example, the setting unit 132 may determine whether or not the normal condition is satisfied by combining the normal conditions (5) to (6).

When the determined behavior of the occupant satisfies the normal condition ("YES" in step ST312), the setting unit 132 sets the state of the occupant to the normal state (step ST313).

On the other hand, when the determined behavior of the occupant does not satisfy the normal condition ("NO" in step ST312), the setting unit 132 sets the state of the occupant to the abnormal state (step ST314).

As described above, when determining that it is necessary to check the state of the occupant on the basis of the plurality of estimation results of the state of the occupant collected from the occupant state estimating device 2, the adjustment device 1 determines the behavior of the occupant and sets the set occupant state. Then, the adjustment device 1 outputs the adjustment information to the occupant state estimating device 2. When the adjustment information is output from the adjustment device 1, the occupant state estimating device 2 adjusts the state estimation condition on the basis of the adjustment information so that the state of the occupant is estimated to be the set occupant state included in the adjustment information in the method for estimating the state of the occupant estimated as the estimation result included in the adjustment information.

As a result, the adjustment device 1 can adjust the method for estimating the state of the occupant in the occupant state estimating device 2 according to the occupant.

Figure 6A:
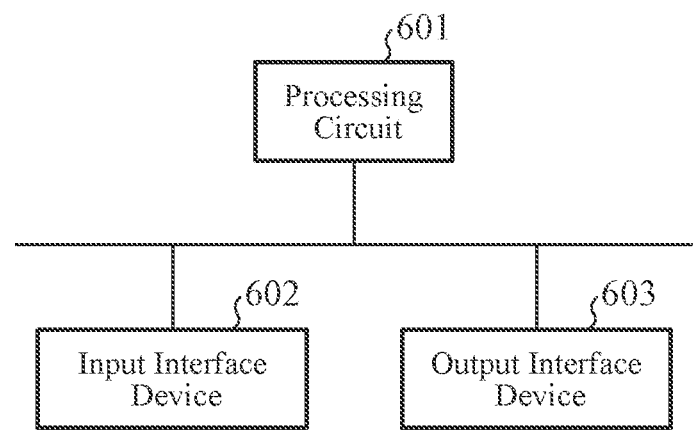
FIGS. 6A and 6B are diagrams illustrating an example of a hardware configuration of the adjustment device according to the first embodiment.
Figure 6B:
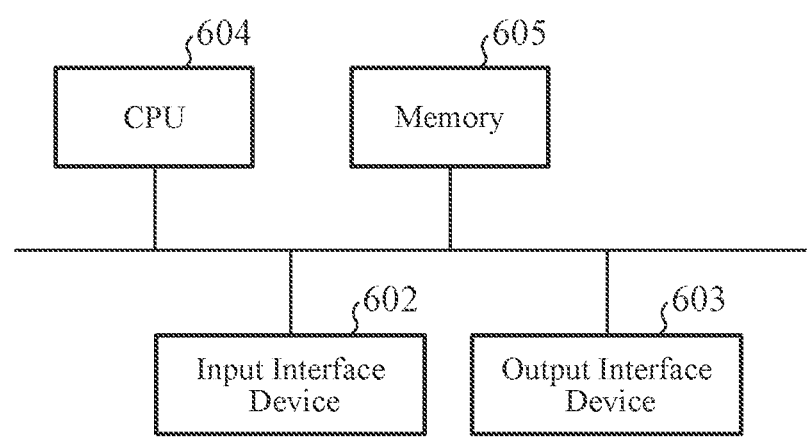

FIGS. 6A and 6B are diagrams illustrating an example of a hardware configuration of the adjustment device 1 according to the first embodiment.

In the first embodiment, the functions of the estimated information collecting unit 11, the determination unit 12, the state checking unit 13, and the adjustment information output unit 14 are implemented by a processing circuit 601. That is, the adjustment device 1 includes the processing circuit 601 for adjusting the method for estimating the state of the occupant in the occupant state estimating device 2 on the basis of the estimation result of the state of the occupant estimated by the occupant state estimating device 2.

The processing circuit 601 may be dedicated hardware as illustrated in FIG. 6A, or may be a central processing unit (CPU) 604 that executes a program stored in a memory 605 as illustrated in FIG. 6B.

In a case where the processing circuit 601 is dedicated hardware, the processing circuit 601 corresponds to, for example, a single circuit, a composite circuit, a programmed processor, a parallel programmed processor, an application specific integrated circuit (ASIC), a field-programmable gate array (FPGA), or a combination thereof.

In a case where the processing circuit 601 is the CPU 604, the functions of the estimated information collecting unit 11, the determination unit 12, the state checking unit 13, and the adjustment information output unit 14 are implemented by software, firmware, or a combination of software and firmware. Software or firmware is described as a program and stored in the memory 605. The processing circuit 601 reads and executes the program stored in the memory 605, thereby executing the functions of the estimated information collecting unit 11, the determination unit 12, the state checking unit 13, and the adjustment information output unit 14. That is, the adjustment device 1 includes the memory 605 for storing a program that results in execution of steps ST1 to ST4 of FIG. 2 described above when executed by the processing circuit 601. In addition, it can also be said that the program stored in the memory 605 causes a computer to execute a procedure or a method performed in the estimated information collecting unit 11, the determination unit 12, the state checking unit 13, and the adjustment information output unit 14. Here, the memory 605 corresponds to, for example, a nonvolatile or volatile semiconductor memory such as a RAM, a read only memory (ROM), a flash memory, an erasable programmable read only memory (EPROM), or an electrically erasable programmable read only memory (EEPROM), or a magnetic disk, a flexible disk, an optical disk, a compact disk, a mini disk, a digital versatile disc (DVD), or the like.

Note that some of the functions of the estimated information collecting unit 11, the determination unit 12, the state checking unit 13, and the adjustment information output unit 14 may be implemented by dedicated hardware, and some thereof may be implemented by software or firmware. For example, the functions of the estimated information collecting unit 11 and the adjustment information output unit 14 can be implemented by the processing circuit 601 as dedicated hardware, and the functions of the determination unit 12 and the state checking unit 13 can be implemented by the processing circuit 601 reading and executing a program stored in the memory 605.

In addition, the storage unit (not illustrated) uses the memory 605. Note that this is an example, and the storage unit may be configured by an HDD, a solid state drive (SSD), a DVD, or the like.

Further, the adjustment device 1 includes an input interface device 602 and an output interface device 603 that perform wired communication or wireless communication with a device such as the occupant state estimating device 2, the driving support device 3, or the behavior determination information collecting device 4.

In the first embodiment described above, the adjustment device 1 is an in-vehicle device mounted on a vehicle, and the estimated information collecting unit 11, the determination unit 12, the state checking unit 13, and the adjustment information output unit 14 are provided in the adjustment device 1. Alternatively, some of the estimated information collecting unit 11, the determination unit 12, the state checking unit 13, and the adjustment information output unit 14 may be included in an in-vehicle device of a vehicle, and the others may be included in a server connected to the in-vehicle device via a network. Further, the occupant state estimating device 2 may be mounted on a server.

In addition, in the first embodiment described above, the occupant is a driver of the vehicle, but this is merely an example. The occupant may be, for example, an occupant other than the driver of the vehicle. For example, the occupant may be a passenger with the driver, or may be an occupant who may take over driving from autonomous driving to manual driving when the vehicle is a vehicle capable of autonomous driving.

In this case, the occupant state estimating device 2 estimates, for example, whether the occupant is in a "normal state" in which the physical condition is good or an "abnormal state" such as poor physical condition or drunken state.

As described above, according to the first embodiment, the adjustment device 1 includes: the estimated information collecting unit 11 to collect estimation results of the state of the occupant estimated by the plurality of occupant state estimating devices 2; the determination unit 12 to determine whether or not it is necessary to check the state of the occupant on the basis of the estimation results collected by the estimated information collecting unit 11; the state checking unit 13 to determine a behavior of the occupant on the basis of behavior determination information for determining a behavior of the occupant and set the state of the occupant when the determination unit 12 determines that it is necessary to check the state of the occupant; and the adjustment information output unit 14 to output adjustment information for causing the occupant state estimating device 2 to adjust a state estimation condition used for estimating the state of the occupant so that the estimation result of the state of the occupant becomes the state of the occupant set by the state checking unit 13. Therefore, the adjustment device 1 can adjust a method for estimating the state of the occupant in the occupant state estimating device that estimates the state of the occupant.

Second Embodiment

In the first embodiment, in the determination processing, the adjustment device determines that it is necessary to check the state of the occupant when at least one of the plurality of collected estimation results indicates the abnormal state, there is an estimation result indicating the normal state among the other estimation results, and there is an estimation result indicating the abnormal state among the estimation results indicating the abnormal state continuously for the determination period.

In a second embodiment, an embodiment in which the determination period is shortened according to the situation will be described.

Figure 7:
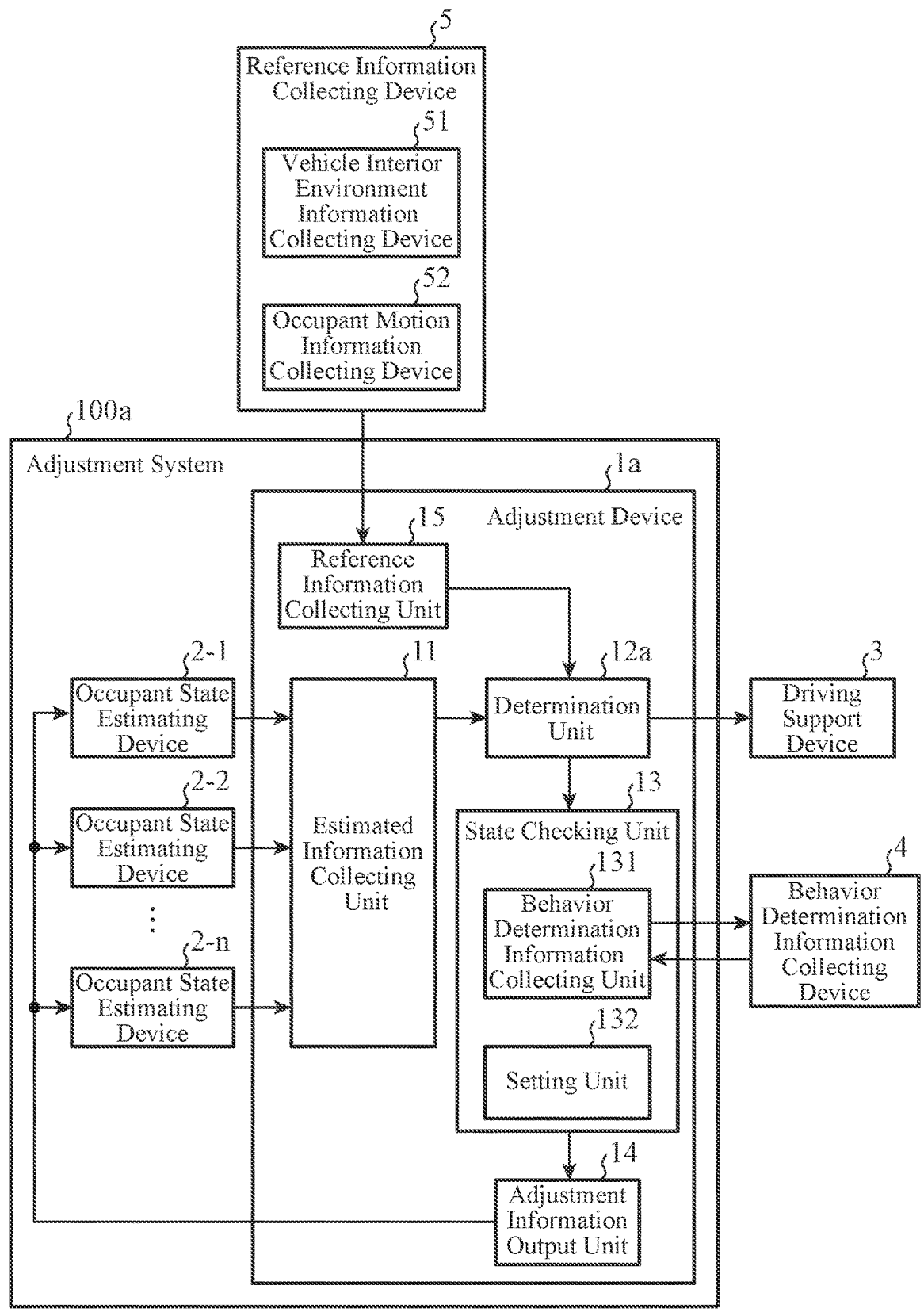
FIG. 7 is a diagram illustrating a configuration example of an adjustment device according to a second embodiment.

FIG. 7 is a diagram illustrating a configuration example of an adjustment device 1a according to the second embodiment.

In the configuration of the adjustment device 1a according to the second embodiment, the same components as those of the adjustment device 1 described with reference to FIG. 1 in the first embodiment are denoted by the same reference numerals, and redundant description will be omitted.

The adjustment device 1a according to the second embodiment is different from the adjustment device 1 according to the first embodiment in that a reference information collecting unit 15 is provided. Further, the specific operation of a determination unit 12a in the adjustment device 1a according to the second embodiment is different from the specific operation of the determination unit 12 in the adjustment device 1 according to the first embodiment.

In the second embodiment, the adjustment device 1a and the occupant state estimating device 2 constitute an adjustment system 100a.

In addition, in the second embodiment, the adjustment device 1a is connected to a reference information collecting device 5.

The reference information collecting device 5 collects information (hereinafter, referred to as "reference information") serving as a reference for determining whether it is necessary to shorten a determination period for determining the duration of the abnormal state indicated by the estimation result in the "determination processing" by the adjustment device 1a.

For example, when the abnormal state is likely, it is possible to shorten the time until the adjustment information is output by promptly checking the state of the occupant without waiting for determination of the abnormal state during the determination period. If the time until the adjustment information is output can be shortened, as a result, the adjustment of the method for estimating the state of the occupant in the occupant state estimating device 2 can be performed quickly.

That is, the reference information is information for estimating the probability of the abnormal state indicated by the estimation result, which is used as a reference for determining whether the adjustment of the method for estimating the state of the occupant in the occupant state estimating device 2 can be performed quickly.

The state of the occupant depends on the environment in the vehicle. For example, when the environment in the vehicle is an environment that causes an abnormality for the occupant, the occupant is likely to be in an abnormal state. The environment in which the environment in the vehicle causes abnormality for the occupant is, for example, an environment in which the oxygen concentration in the air in the vehicle is low or the carbon dioxide concentration is high.

In addition, for example, there is a motion (hereinafter, referred to as "abnormal-time motion") that is likely to be performed when the occupant is in an abnormal state. For example, when the occupant is in a non-awakening state, the occupant performs a motion for maintaining awakening, such as pinching the body to awaken.

Therefore, the probability of the abnormal state of the occupant can be estimated from the environment in the vehicle or whether or not the occupant is performing the abnormal-time motion.

Therefore, in the second embodiment, the reference information is information for determining the environment in the vehicle (hereinafter, referred to as "vehicle interior environment determination information") or information for determining the occupant's abnormal-time motion (hereinafter, referred to as "abnormal-time motion determination information").

Specific examples of the vehicle interior environment determination information include information indicating a substance concentration in the air in the vehicle, a temperature in the vehicle, humidity in the vehicle, or a continuous driving time. The substance concentration in the air in the vehicle is, for example, an oxygen concentration or a carbon dioxide concentration.

Specific examples of the abnormal-time motion determination information include a vehicle interior captured image, a steering wheel operation amount, pressure applied to a steering wheel, seat pressure of a seat, and seat belt wearing information.

The reference information collecting device 5 is various devices capable of collecting reference information.

The reference information collecting device 5 includes a vehicle interior environment information collecting device 51 and an occupant motion information collecting device 52. The vehicle interior environment information collecting device 51 collects vehicle interior environment determination information. The vehicle interior environment information collecting device 51 is, for example, a concentration measuring device, a temperature sensor, a humidity sensor, or a navigation device mounted on the vehicle.

The occupant motion information collecting device 52 collects abnormal-time motion determination information. The occupant motion information collecting device 52 is, for example, an in-vehicle camera mounted on a vehicle, a steering angle sensor, a pressure sensor provided on a steering wheel, a seat pressure sensor, or a seat belt sensor.

Note that the reference information collecting device 5 may be a device common to the behavior determination information collecting device 4.

In the adjustment device 1a, the reference information collecting unit 15 collects the reference information from the reference information collecting device 5. Specifically, the reference information collecting unit 15 collects vehicle interior environment determination information from the vehicle interior environment information collecting device 51. Further, the reference information collecting unit 15 collects abnormal-time motion determination information from the occupant motion information collecting device 52.

Note that it is not essential for the reference information collecting unit 15 to collect both the vehicle interior environment determination information and the abnormal-time motion determination information. The reference information collecting unit 15 may collect only one of the vehicle interior environment determination information and the abnormal-time motion determination information.

When the reference information collecting device 5 is a device common to the behavior determination information collecting device 4, the reference information collecting unit 15 collects the vehicle interior environment determination information or the abnormal-time motion determination information from the behavior determination information collecting device 4.

The reference information collecting unit 15 outputs the collected reference information, in other words, the vehicle interior environment determination information or the abnormal-time motion determination information, to the determination unit 12*a*.

The determination unit 12*a* performs "determination processing" on the basis of the plurality of estimation results collected by the estimated information collecting unit 11. At that time, the determination unit 12*a* determines whether or not to shorten the determination period on the basis of the reference information collected by the reference information collecting unit 15. When determining to shorten the determination period, the determination unit 12*a* shortens the determination period and performs "determination processing" using the shortened determination period. Since the "determination processing" performed by the determination unit 12*a* is similar to the "determination processing" described in the first embodiment and performed by the determination unit 12 except that the determination period is shortened, redundant description will be omitted.

The operation of shortening the determination period by the determination unit 12*a* will be described with a specific example.

For example, the determination unit 12*a* shortens the determination period on the basis of the vehicle interior environment determination information depending on whether the environment in the vehicle is an environment that causes an abnormality for the occupant. The determination unit 12*a*, when determining that the environment in the vehicle is an environment that causes an abnormality for the occupant, shortens the determination period. For example, the determination unit 12*a*, when determining that the low frequency vibration is continuously generated in the vehicle, shortens the determination period. In addition, for example, when the oxygen concentration in the vehicle is lower than a preset threshold, the determination unit 12*a* shortens the determination period. Further, for example, when the humidity in the vehicle is higher than a preset threshold, the determination unit 12*a* shortens the determination period.

Furthermore, for example, the determination unit 12*a* shortens the determination period on the basis of whether or not the occupant is performing a motion for maintaining awakening or whether or not there is a change in body motion on the basis of the abnormal-time motion determination information. The determination unit 12*a*, when determining that the occupant is performing a motion for maintaining awakening or that there is a change in body motion, shortens the determination period. For example, when the abnormal-time motion determination information is a vehicle interior captured image, the determination unit 12*a* can determine that the occupant is performing a motion for maintaining awakening using a known image recognition technology. Further, for example, when the abnormal-time motion determination information is the seat pressure or the amount of withdrawal of the seat belt, the determination unit 12*a* can determine whether or not there is a change in the body motion of the occupant from the seat pressure or the amount of withdrawal of the seat belt.

Note that how much the determination unit 12*a* shortens the determination period is determined in advance.

The determination unit 12*a* may change the period to be shortened depending on the degree to which the environment in the vehicle is an environment causing an abnormality for the occupant or the content of the abnormal-time motion performed by the occupant. It is assumed that how much the determination period is shortened in a case where the degree of the environment in the vehicle causing an abnormality for the occupant is how much, and how much the determination period is shortened in a case where the content of the abnormal-time motion performed by the occupant is what kind of content are determined in advance.

By changing the period to be shortened depending on the degree to which the environment in the vehicle is an environment that causes an abnormality for the occupant or the content of the abnormal-time motion performed by the occupant, the adjustment device 1*a* can check the state of the occupant more quickly and shorten the time until the adjustment information is output when the abnormal state is more likely than when the period to be shortened is not changed. As a result, the adjustment device 1*a* can adjust the method for estimating the state of the occupant in the occupant state estimating device 2 more quickly.

The operation of the adjustment device 1*a* according to the second embodiment will be described.

Figure 8:
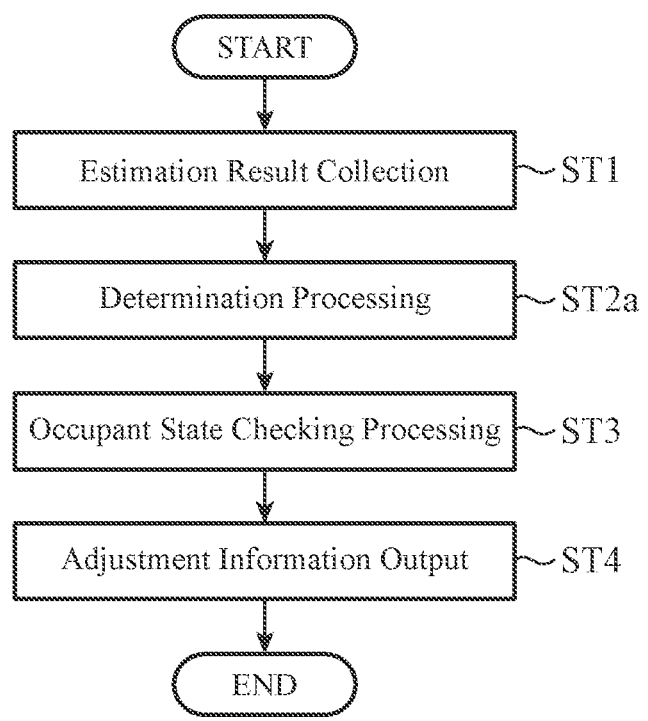
FIG. 8 is a flowchart for explaining an operation of the adjustment device according to the second embodiment.

FIG. 8 is a flowchart for explaining the operation of the adjustment device 1*a* according to the second embodiment.

Specific operations of step ST1 and steps ST3 to ST4 in FIG. 8 are similar to the specific operations of step ST1 and steps ST3 to ST4 in FIG. 2 by the adjustment device 1 according to the first embodiment, which have been described in the first embodiment, respectively, and thus redundant description will be omitted.

The determination unit 12*a* performs "determination processing" on the basis of the plurality of estimation results collected by the estimated information collecting unit 11 in step ST1 of FIG. 8 (step ST2*a*).

Figure 9:
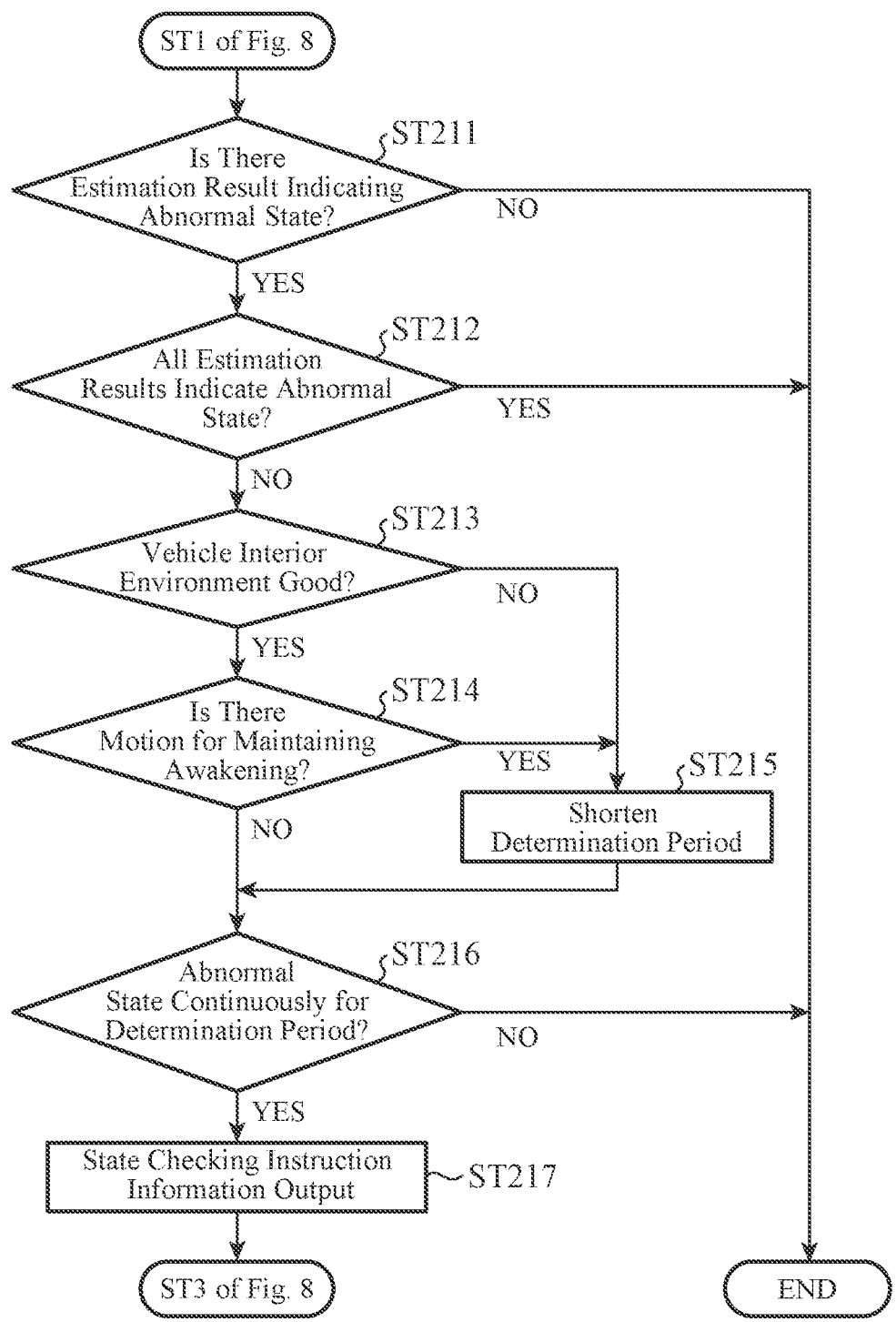
FIG. 9 is a flowchart for explaining details of "determination processing" by a determination unit in step ST2*a* in FIG. 8.

FIG. 9 is a flowchart for explaining details of the "determination processing" by the determination unit 12*a* in step ST2*a* in FIG. 8.

In FIG. 9, specific operations in steps ST211 to ST212 and steps ST216 to ST217 are similar to the specific operations in steps ST201 to ST204 in FIG. 3, which have been described in the first embodiment, respectively, and thus redundant description will be omitted.

When it is determined in step ST212 that not all the estimation results are estimation results indicating an abnormal state, in other words, when there is an estimation result indicating a normal state among other estimation results ("NO" in step ST212), the reference information collecting unit 15 collects reference information from the reference information collecting device 5. Then, the determination unit 12*a* determines whether or not the environment in the vehicle is good, in other words, whether or not the environment in the vehicle is an environment causing abnormality for the occupant, on the basis of the reference information collected by the reference information collecting unit 15, more specifically, the vehicle interior environment determination information (step ST213).

When it is determined in step ST213 that the environment in the vehicle is good, in other words, when it is determined that the environment in the vehicle is not an environment that causes an abnormality for the occupant ("YES" in step ST213), the determination unit 12*a* determines whether or not the occupant is performing a motion for maintaining awakening on the basis of the reference information, more specifically, the abnormal-time motion determination information (step ST214).

When it is determined in step ST214 that the occupant is not performing the motion for maintaining awakening ("NO" in step ST214), the operation of the determination unit 12*a* proceeds to the operation of step ST216.

On the other hand, when it is determined in step ST213 that the environment in the vehicle is not good, in other words, when it is determined that the environment in the vehicle is an environment that causes an abnormality for the occupant ("NO" in step ST213), and when it is determined in step ST214 that the occupant is performing a motion for maintaining awakening ("YES" in step ST214), the determination unit 12a shortens the determination period. Then, the operation of the determination unit 12a proceeds to the operation of step ST216.

Note that, here, the determination unit 12a determines whether or not the occupant is performing the motion for maintaining awakening in step ST214, but this is merely an example. In step ST214, the determination unit 12a may determine, for example, whether or not there is a change in the body motion of the occupant. In step ST214, it is sufficient that the determination unit 12a determines whether or not the occupant is performing the abnormal-time motion.

In addition, here, the operation is performed in the order of step ST213 and step ST214, but the order of step ST213 and step ST214 may be reversed.

Furthermore, for example, in a case where the reference information collecting unit 15 does not collect the vehicle interior environment determination information, the determination unit 12a can omit the operation of step ST213. Furthermore, for example, in a case where the reference information collecting unit 15 does not collect the abnormal-time motion determination information, the determination unit 12a can omit the operation of step ST214.

As described above, when the abnormal state estimated by the occupant state estimating device 2 is likely, the adjustment device 1a shortens the determination period. As a result, the adjustment device 1a can shorten the time until the adjustment information is output by quickly checking the state of the occupant. As a result, the adjustment device 1a can quickly adjust the method for estimating the state of the occupant in the occupant state estimating device 2.

Since the hardware configuration of the adjustment device 1a according to the second embodiment is similar to the hardware configuration of the adjustment device 1 according to the first embodiment described with reference to FIGS. 6A and 6B, illustration thereof is omitted.

In the second embodiment, the functions of the estimated information collecting unit 11, the determination unit 12a, the state checking unit 13, the adjustment information output unit 14, and the reference information collecting unit 15 are implemented by the processing circuit 601. That is, the adjustment device 1a includes the processing circuit 601 for adjusting the method for estimating the state of the occupant in the occupant state estimating device 2 on the basis of the estimation result of the state of the occupant estimated by the occupant state estimating device 2.

The processing circuit 601 reads and executes the program stored in the memory 605, thereby executing the functions of the estimated information collecting unit 11, the determination unit 12a, the state checking unit 13, the adjustment information output unit 14, and the reference information collecting unit 15. That is, the adjustment device 1a includes the memory 605 for storing a program that results in execution of steps ST1 to ST4 of FIG. 8 described above when executed by the processing circuit 601. In addition, it can also be said that the program stored in the memory 605 causes a computer to execute a procedure or a method performed in the estimated information collecting unit 11, the determination unit 12a, the state checking unit 13, the adjustment information output unit 14, and the reference information collecting unit 15.

The adjustment device 1a includes the input interface device 602 and the output interface device 603 that perform wired communication or wireless communication with a device such as the occupant state estimating device 2, the driving support device 3, the behavior determination information collecting device 4, or the reference information collecting device.

In the adjustment device 1a according to the second embodiment described above, some of the estimated information collecting unit 11, the determination unit 12a, the state checking unit 13, the adjustment information output unit 14, and the reference information collecting unit 15 may be included in an in-vehicle device of a vehicle, and the others may be included in a server connected to the in-vehicle device via a network. Further, the occupant state estimating device 2 may be mounted on a server.

In addition, also in the second embodiment described above, as in the first embodiment, the occupant may be, for example, an occupant other than the driver of the vehicle.

As described above, according to the second embodiment, the adjustment device 1a includes the reference information collecting unit 15 to collect, as reference information, at least one of vehicle interior environment determination information for determining an environment in a vehicle and abnormal-time motion determination information for determining a motion that the occupant tends to perform in a case where the occupant is in an abnormal state, and the determination unit 12a is configured to shorten the determination period on the basis of the reference information collected by the reference information collecting unit 15. Therefore, the adjustment device 1a can adjust the method for estimating the state of the occupant in the occupant state estimating device that estimates the state of the occupant, and when the abnormal state estimated by the occupant state estimating device 2 is likely, the adjustment device 1a can quickly adjust the method for estimating the state of the occupant in the occupant state estimating device 2 by shortening the determination period.

Third Embodiment

In the first embodiment, in the "determination processing", the adjustment device determines that it is necessary to check the state of the occupant when there is an estimation result indicating the abnormal state continuously for the determination period among the estimation results indicating the abnormal state.

In a third embodiment, an embodiment in which whether or not it is necessary to check the state of the occupant is determined on the basis of a learned model (hereinafter, referred to as a "machine learning model") in machine learning will be described.

Figure 10:
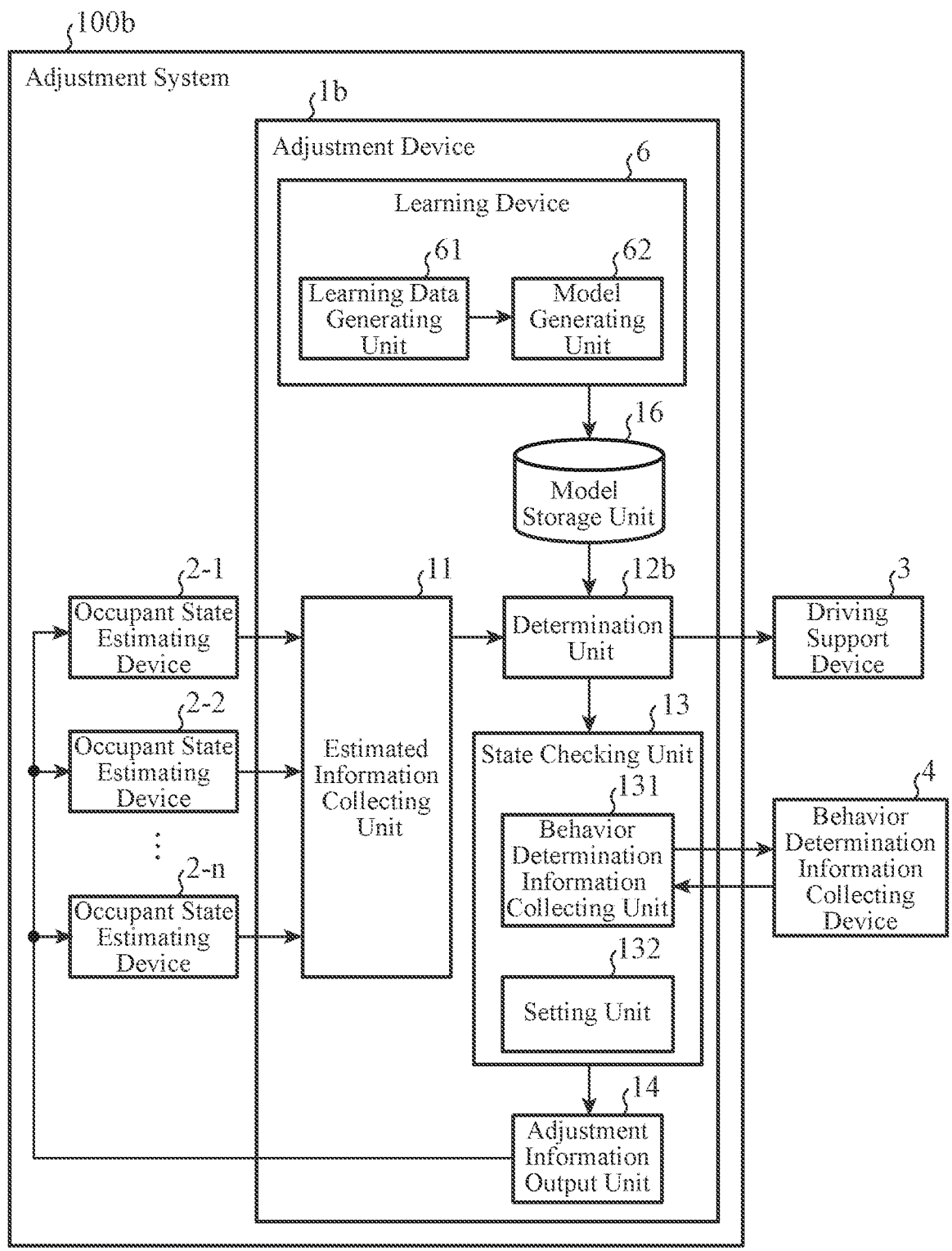
FIG. 10 is a diagram illustrating a configuration example of an adjustment device according to a third embodiment.

FIG. 10 is a diagram illustrating a configuration example of an adjustment device 1b according to the third embodiment.

In the configuration of the adjustment device 1b according to the third embodiment, the same components as those of the adjustment device 1 described with reference to FIG. 1 in the first embodiment are denoted by the same reference numerals, and redundant description will be omitted.

The adjustment device 1b according to the third embodiment is different from the adjustment device 1 according to the first embodiment in that a learning device 6 is mounted and a model storage unit 16 is provided. Further, the specific operation of a determination unit 12b in the adjustment device 1b according to the third embodiment is different from the specific operation of the determination unit 12 in the adjustment device 1 according to the first embodiment.

In the third embodiment, the adjustment device 1*b* and the occupant state estimating device 2 constitute an adjustment system 100*b*.

In the "determination processing", the determination unit 12*b* determines whether or not it is necessary to check the state of the occupant on the basis of the estimation result collected by the estimated information collecting unit 11 and the machine learning model.

The machine learning model is a machine learning model that uses the estimation result of the state of the occupant as an input and outputs information (hereinafter, referred to as "checking necessity information") indicating whether or not it is necessary to check the state of the occupant. The checking necessity information is represented by, for example, "1 (checking necessary)" or "0 (checking unnecessary)".

The machine learning model is generated by the learning device 6 by so-called supervised learning and stored in the model storage unit 16.

The determination unit 12*b* acquires the machine learning model from the model storage unit 16, and performs "determination processing" on the basis of the estimation result collected by the estimated information collecting unit 11 and the machine learning model. Specifically, the determination unit 12*b* uses the estimation result collected by the estimated information collecting unit 11 as an input of the machine learning model, and obtains checking necessity information output from the machine learning model.

When obtaining the checking necessity information indicating that the checking is necessary, the determination unit 12*b* determines that it is necessary to check the state of the occupant. On the other hand, when obtaining the checking necessity information indicating that the checking is unnecessary, the determination unit 12*b* determines that it is not necessary to check the state of the occupant.

Note that when the machine learning model is not stored in the model storage unit 16, the determination unit 12*b* determines whether or not it is necessary to check the state of the occupant by a method similar to that of the first embodiment, specifically, by determining whether or not there is an estimation result indicating an abnormal state continuously during the determination period among the estimation results indicating an abnormal state.

A configuration example of the learning device 6 will be described.

The learning device 6 includes a learning data generating unit 61 and a model generating unit 62.

The learning data generating unit 61 generates learning data for generating a machine learning model. Specifically, the learning data generating unit 61 generates learning data including the estimation result of the state of the occupant and the checking necessity information. The checking necessity information is a teacher label.

In the adjustment device 1*b* according to the third embodiment, the estimated information collecting unit 11 stores a plurality of collected estimation results in a storage unit (not illustrated). In addition, the determination unit 12*b* sets checking necessity information on the basis of a result of whether or not it is determined that the state of the occupant needs to be checked at the time of performing the "determination processing", and stores the set checking necessity information in the storage unit. For example, the determination unit 12*b* sets and stores checking necessity information of "1 (checking necessary)" in a case where it is determined that the state of the occupant needs to be checked, and sets and stores checking necessity information of "0 (checking unnecessary)" in a case where it is determined that the state of the occupant does not need to be checked. The determination unit 12*b* stores the checking necessity information in association with a plurality of corresponding estimation results, that is, a plurality of estimation results used in the "determination processing".

The learning data generating unit 61 acquires the estimation result of the state of the occupant collected from the occupant state estimating device 2 by the estimated information collecting unit 11 and the checking necessity information set by the determination unit 12*b*, which are stored in the storage unit in association with each other, and generates learning data in which the acquired estimation result and the checking necessity information are associated with each other.

Note that the learning data generating unit 61 generates learning data when a preset number of associated estimation results and set occupant states are stored.

The learning data generating unit 61 outputs the generated learning data to the model generating unit 62.

The model generating unit 62 generates a machine learning model on the basis of the learning data generated by the learning data generating unit 61.

As a learning algorithm used by the model generating unit 62, a known algorithm of supervised learning can be used. As an example, a case where a neural network is used for a learning algorithm will be described.

For example, the model generating unit 62 learns whether or not it is necessary to check the state of the occupant by so-called supervised learning according to the neural network model. Here, the supervised learning refers to a technique of giving a set of data of an input and a result (teacher label) to a learning device to learn features in the learning data and to infer a result from the input. The neural network includes an input layer including a plurality of neurons, an intermediate layer (hidden layer) including a plurality of neurons, and an output layer including a plurality of neurons. The intermediate layer may be one layer or two or more layers.

Figure 11:
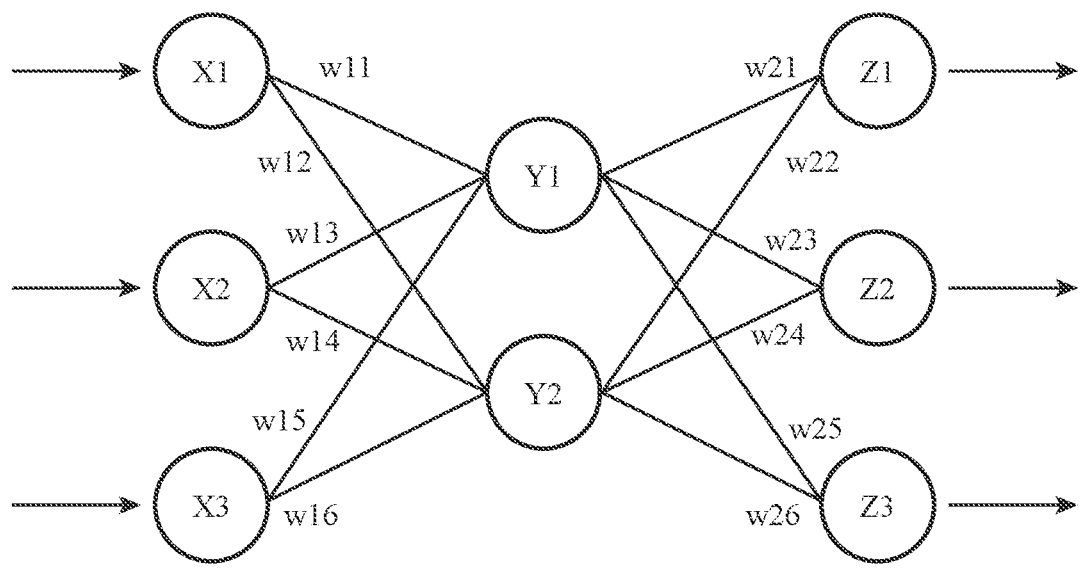
FIG. 11 is a diagram for explaining a neural network.

Here, FIG. 11 is a diagram for describing a neural network.

For example, in the case of a three-layer neural network as illustrated in FIG. 11, when a plurality of inputs are input to the input layer (X1-X3), the value is multiplied by a weight W1 ($w11$-$w16$) and input to the intermediate layer (Y1-Y2), and the result is further multiplied by a weight W2 ($w21$-$w26$) and output from the output layer (Z1-Z3). This output result varies depending on the values of the weights W1 and W2.

The model generating unit 62 causes a machine learning model configured by a neural network to learn by so-called supervised learning according to learning data generated on the basis of a combination of the estimation result collected by the estimated information collecting unit 11 and the checking necessity information.

The model generating unit 62 stores the generated machine learning model in the model storage unit 16.

Note that, as described above, the learning data is not generated until a preset number of associated estimation results and set occupant states are stored. Therefore, the machine learning model is not generated until a preset number of associated estimation results and set occupant states are stored. During this time, the determination unit 12*b* determines whether or not it is necessary to check the state of the occupant depending on whether or not there is an estimation result indicating an abnormal state continuously for the determination period among the estimation results indicating an abnormal state.

The model storage unit 16 stores the machine learning model generated by the model generating unit 62.

Note that, here, the model storage unit 16 is provided in the adjustment device 1*b*, but this is merely an example. The model storage unit 16 may be provided outside the adjustment device 1*b* at a place that can be referred to by the adjustment device 1*b*.

The operation of the adjustment device 1*b* according to the third embodiment will be described.

Figure 12:
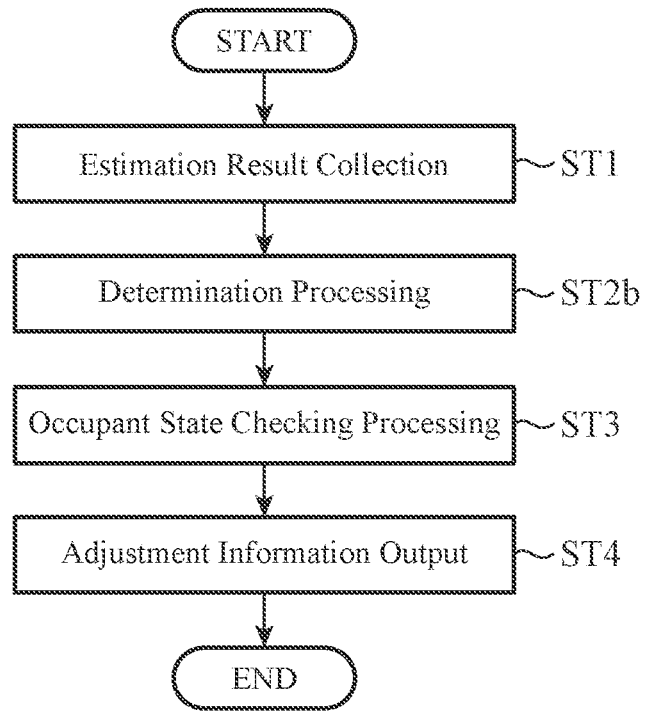
FIG. 12 is a flowchart for explaining an operation of the adjustment device according to the third embodiment.

FIG. 12 is a flowchart for explaining the operation of the adjustment device 1*b* according to the third embodiment.

Note that the operation of the adjustment device 1*b* described in the flowchart of FIG. 12 is based on the assumption that a machine learning model is generated by the learning device 6 and the machine learning model is stored in the model storage unit 16. When the machine learning model is not generated, the adjustment device 1*b* performs the same operation as the operation of the adjustment device 1 described with reference to the flowchart of FIG. 2 in the first embodiment.

The specific operations in step ST1 and steps ST3 to ST4 in FIG. 12 are similar to the specific operations in step ST1 and steps ST3 to ST4 in FIG. 2 by the adjustment device 1 according to the first embodiment, which have been described in the first embodiment, respectively, and thus redundant description will be omitted.

The determination unit 12*b* performs "determination processing" on the basis of the plurality of estimation results collected by the estimated information collecting unit 11 in step ST1 and the machine learning model (step ST2*b*).

Figure 13:
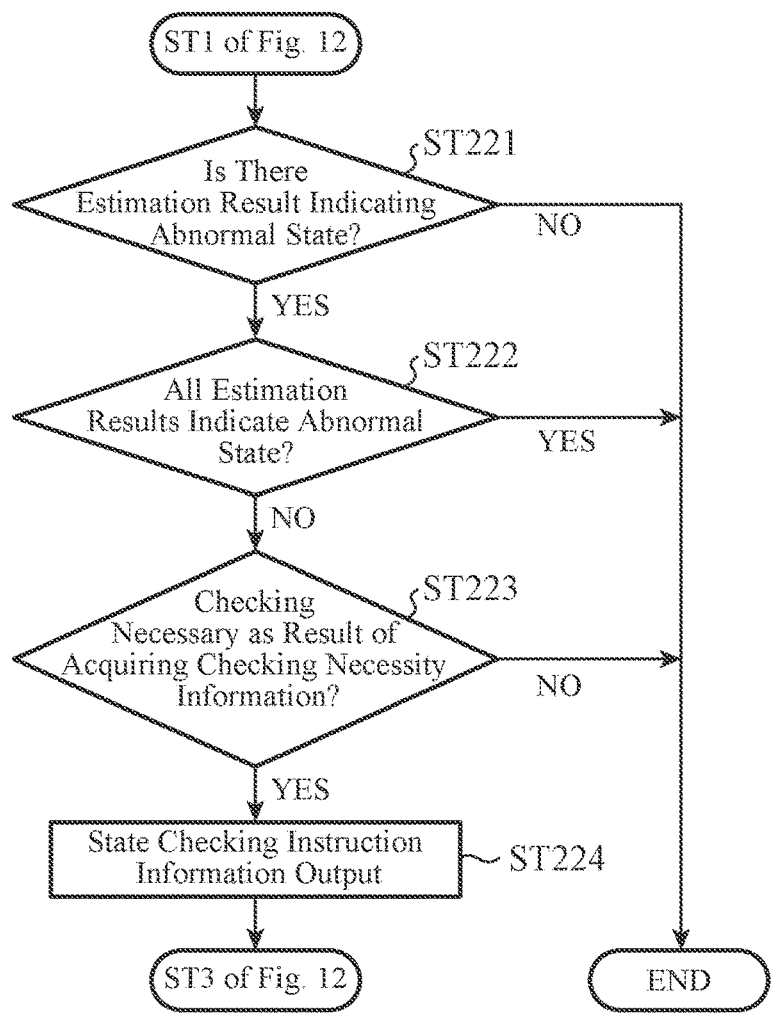
FIG. 13 is a flowchart for explaining details of "determination processing" by the determination unit in step ST2*b* in FIG. 12.

FIG. 13 is a flowchart for explaining details of "determination processing" by the determination unit 12*b* in step ST2*b* in FIG. 12.

In FIG. 13, the specific operations in steps ST221 to ST222 and step ST224 are similar to the specific operations in steps ST201 to ST202 and step ST204 in FIG. 3 described in the first embodiment, respectively, and thus redundant description will be omitted.

When it is determined in step ST222 that not all of the estimation results are estimation results indicating an abnormal state, in other words, when there is an estimation result indicating a normal state among other estimation results ("NO" in step ST222), the determination unit 12*b* uses the estimation result collected by the estimated information collecting unit 11 in ST1 of FIG. 12 as an input of the machine learning model, and obtains checking necessity information output from the machine learning model.

When obtaining the checking necessity information indicating that the checking is necessary ("YES" in step ST223), the determination unit 12*b* determines that it is necessary to check the state of the occupant. Then, the operation of the determination unit 12*b* proceeds to step ST224.

On the other hand, when obtaining the checking necessity information indicating that the checking is unnecessary ("NO" in step ST223), the determination unit 12*b* determines that it is not necessary to check the state of the occupant. Then, the adjustment device 1*b* ends the operation illustrated in the flowchart of FIG. 12.

In this manner, the adjustment device 1*b* determines whether or not it is necessary to check the state of the occupant on the basis of the plurality of estimation results of the state of the occupant collected from the occupant state estimating device 2 and the machine learning model.

As a result, since the adjustment device 1*b* does not need to wait for the determination period when determining whether or not to check the state of the occupant, it is possible to shorten the time required for the "determination processing" as compared with the adjustment device 1 according to the first embodiment. As a result, the adjustment device 1*b* can adjust the method for estimating the state of the occupant in the occupant state estimating device 2 more quickly than the adjustment device 1 according to the first embodiment, in other words, as compared with the case of waiting for the determination period when determining whether or not to check the state of the occupant.

The operation of the learning device 6 according to the third embodiment will be described.

Figure 14:
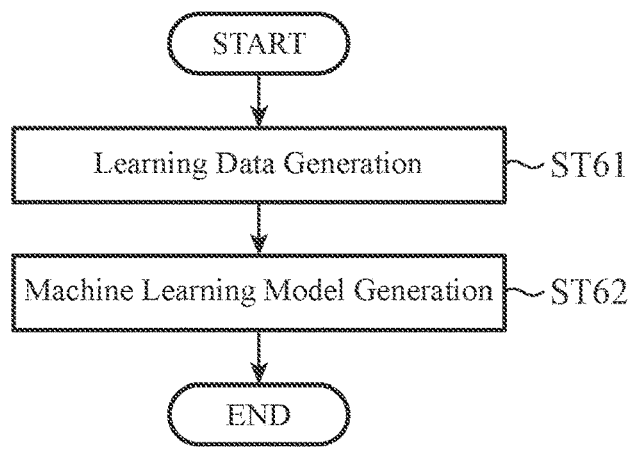
FIG. 14 is a flowchart for explaining an operation of a learning device according to the third embodiment.

FIG. 14 is a flowchart for explaining the operation of the learning device 6 according to the third embodiment. While the vehicle is traveling, the operation shown in the flowchart of FIG. 14 is repeated.

The learning data generating unit 61 generates learning data in which the estimation result is associated with the checking necessity information (step ST61).

The learning data generating unit 61 outputs the generated learning data to the model generating unit 62.

The model generating unit 62 generates a machine learning model on the basis of the learning data generated by the learning data generating unit 61 in step ST61 (step ST62).

The model generating unit 62 stores the generated machine learning model in the model storage unit 16.

As described above, the learning device 6 repeats the operation illustrated in the flowchart of FIG. 14 while the vehicle is traveling. That is, the learning device 6 continues to update the machine learning model while the vehicle is traveling. As a result, the learning device 6 can improve the accuracy of the machine learning model.

In addition, while the vehicle is traveling, the adjustment device 1*b* performs determination processing on the basis of the machine learning model with improved accuracy, thereby improving the accuracy of determination as to whether or not it is necessary to check the state of the occupant.

Note that in the third embodiment, it is assumed that the learning device 6 is mounted on the adjustment device 1*b*, but this is merely an example. The learning device 6 may be provided outside the adjustment device 1*b* at a place that can be referred to by the adjustment device 1*b*.

In addition, in the third embodiment described above, the learning device 6 generates the machine learning model from the plurality of estimation results collected while the vehicle is traveling and the checking necessity information set while the vehicle is traveling. The present disclosure is not limited thereto, and for example, a machine learning model as an initial value may be generated in advance or at the time when driving of the vehicle is started and stored in the model storage unit 16. In this case, for example, the learning device 6 generates a machine learning model on the basis of learning data generated in advance on the basis of a plurality of estimation results of the state of the occupant collected by simulation traveling or the like and checking necessity information associated with the estimation results, and stores the machine learning model in the model storage unit 16. Note that, in this case, the learning data generating unit 61 may acquire learning data generated in advance, or may generate learning data from a plurality of estimation results of the state of the occupant collected by simulation traveling or the like and checking necessity information associated with the estimation results.

Since the hardware configuration of the adjustment device 1*b* according to the third embodiment is similar to the hardware configuration of the adjustment device 1 according to the first embodiment described with reference to FIGS. 6A and 6B, illustration thereof is omitted.

In the third embodiment, the functions of the estimated information collecting unit 11, the determination unit 12b, the state checking unit 13, and the adjustment information output unit 14 are implemented by the processing circuit 601. That is, the adjustment device 1b includes the processing circuit 601 for adjusting the method for estimating the state of the occupant in the occupant state estimating device 2 on the basis of the estimation result of the state of the occupant estimated by the occupant state estimating device 2.

The processing circuit 601 reads and executes the program stored in the memory 605, thereby executing the functions of the estimated information collecting unit 11, the determination unit 12b, the state checking unit 13, and the adjustment information output unit 14. That is, the adjustment device 1b includes the memory 605 for storing a program that results in execution of steps ST1 to ST4 of FIG. 12 described above when executed by the processing circuit 601. In addition, it can also be said that the program stored in the memory 605 causes a computer to execute a procedure or a method performed in the estimated information collecting unit 11, the determination unit 12b, the state checking unit 13, and the adjustment information output unit 14.

In addition, the model storage unit 16 uses the memory 605. Note that this is an example, and the model storage unit 16 may be configured by an HDD, an SSD, a DVD, or the like.

The adjustment device 1b includes the input interface device 602 and the output interface device 603 that perform wired communication or wireless communication with a device such as the occupant state estimating device 2, the driving support device 3, or the behavior determination information collecting device 4.

Figure 15A:
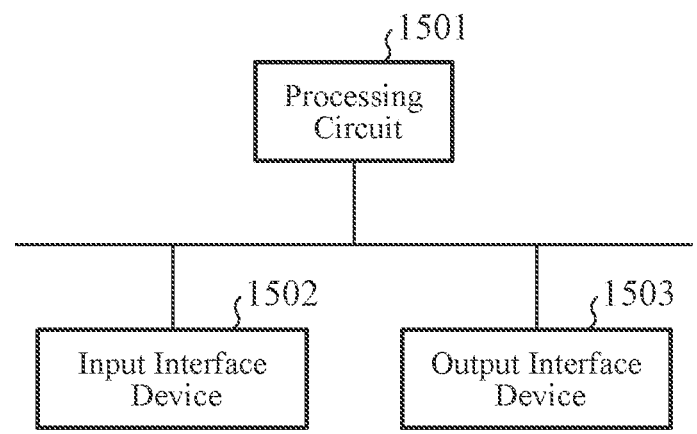
FIGS. 15A and 15B are diagrams illustrating an example of a hardware configuration of the learning device according to the third embodiment.
Figure 15B:
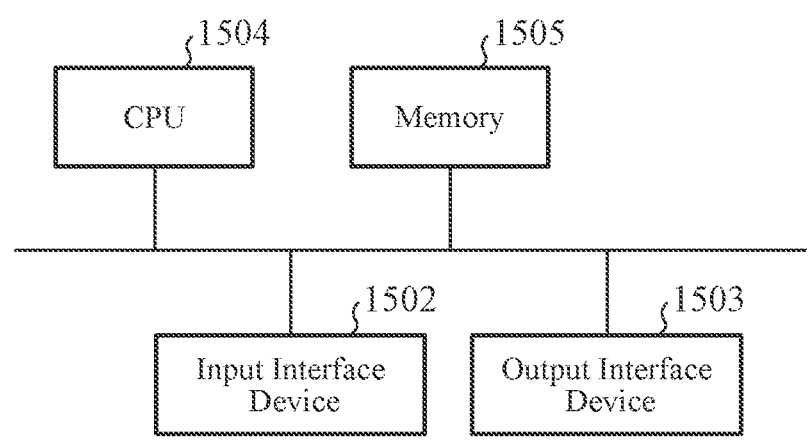

FIGS. 15A and 15B are diagrams illustrating an example of a hardware configuration of the learning device 6 according to the third embodiment.

In the third embodiment, the functions of the learning data generating unit 61 and the model generating unit 62 are implemented by a processing circuit 1501. That is, the learning device 6 includes the processing circuit 1501 for adjusting the method for estimating the state of the occupant in the occupant state estimating device 2 on the basis of the estimation result of the state of the occupant estimated by the occupant state estimating device 2.

The processing circuit 1501 may be dedicated hardware as illustrated in FIG. 15A, or may be a CPU 1504 that executes a program stored in a memory 1505 as illustrated in FIG. 15B.

In a case where the processing circuit 1501 is dedicated hardware, the processing circuit 1501 corresponds to, for example, a single circuit, a composite circuit, a programmed processor, a parallel programmed processor, ASIC, FPGA, or a combination thereof.

When the processing circuit 1501 is the CPU 1504, the functions of the learning data generating unit 61 and the model generating unit 62 are implemented by software, firmware, or a combination of software and firmware. Software or firmware is written as a program and stored in the memory 1505. The processing circuit 1501 executes the functions of the learning data generating unit 61 and the model generating unit 62 by reading and executing the program stored in the memory 1505. That is, the learning device 6 includes the memory 1505 for storing a program that results in execution of steps ST61 to ST62 of FIG. 14 described above when executed by the processing circuit 1501. In addition, it can also be said that the program stored in the memory 1505 causes a computer to execute the procedures or methods performed in the learning data generating unit 61 and the model generating unit 62. Here, the memory 1505 corresponds to, for example, a nonvolatile or volatile semiconductor memory such as RAM, ROM, a flash memory, EPROM, or EEPROM, or a magnetic disk, a flexible disk, an optical disk, a compact disk, a mini disk, DVD, or the like.

Note that the functions of the learning data generating unit 61 and the model generating unit 62 may be partially implemented by dedicated hardware and partially implemented by software or firmware. For example, the function of the learning data generating unit 61 can be implemented by the processing circuit 1501 as dedicated hardware, and the function of the model generating unit 62 can be implemented by the processing circuit 1501 reading and executing a program stored in the memory 1505.

In addition, the storage unit (not illustrated) uses the memory 1505. Note that this is an example, and the storage unit may be configured by an HDD, an SSD, a DVD, or the like.

In addition, the learning device 6 includes an input interface device 1502 and an output interface device 1503 that perform wired communication or wireless communication with a device such as the adjustment device 1b.

In the adjustment device 1b according to the above-described third embodiment, some of the estimated information collecting unit 11, the determination unit 12b, the state checking unit 13, and the adjustment information output unit 14 may be included in an in-vehicle device of a vehicle, and the others may be included in a server connected to the in-vehicle device via a network. Furthermore, in the learning device 6, some of the learning data generating unit 61 and the model generating unit 62 may be included in an in-vehicle device of a vehicle, and the others may be included in a server connected to the in-vehicle device via a network.

The occupant state estimating device 2 may be mounted on a server.

In addition, also in the third embodiment described above, as in the first embodiment, the occupant may be, for example, an occupant other than the driver of the vehicle.

The third embodiment described above may be applied to the adjustment device according to the second embodiment.

Figure 16:
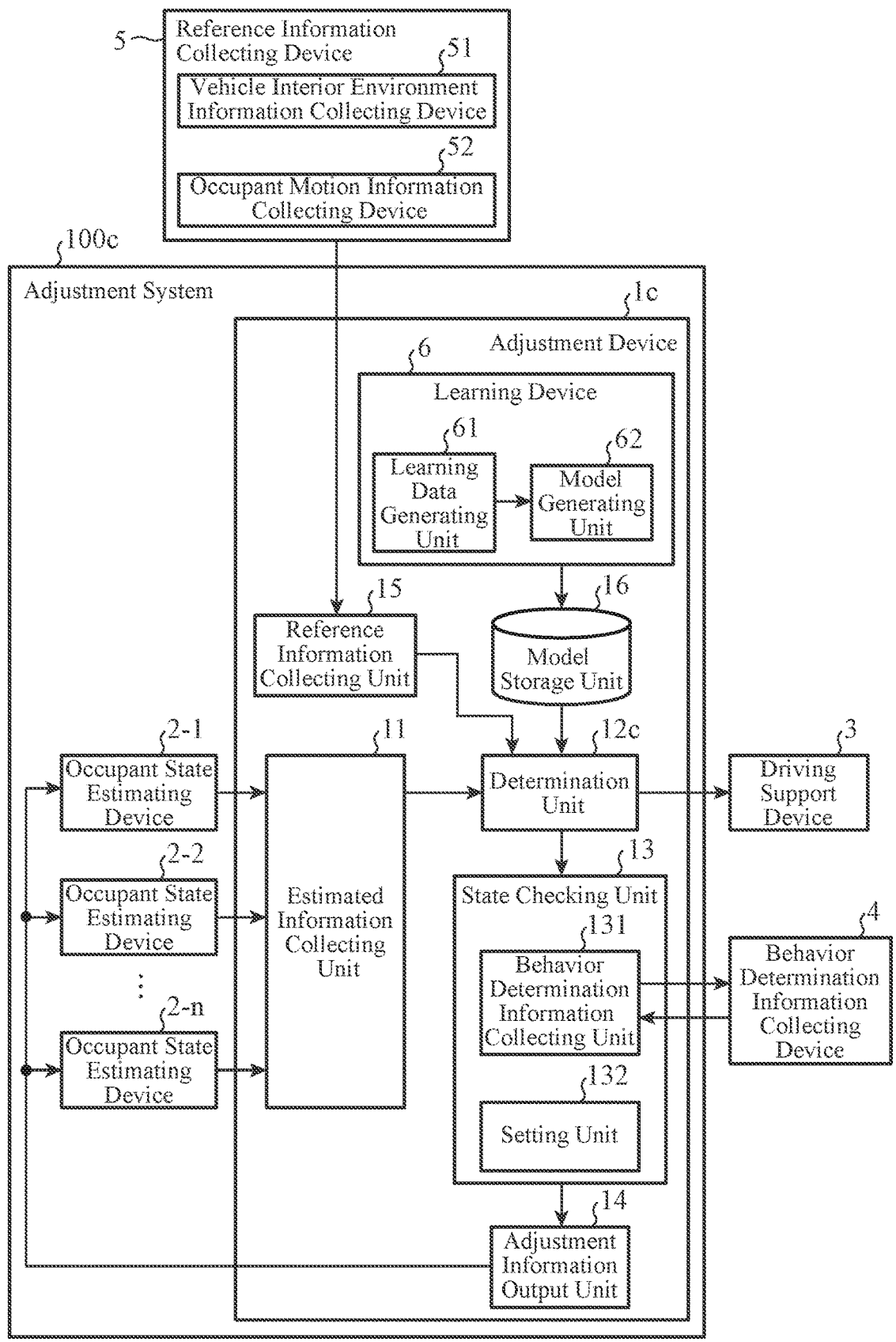
FIG. 16 is a diagram illustrating a configuration example of an adjustment device in a case where the third embodiment is applied to the adjustment device according to the second embodiment.

FIG. 16 is a diagram illustrating a configuration example of an adjustment device 1c in a case where the third embodiment is applied to the adjustment device according to the second embodiment.

In the configuration of the adjustment device 1c illustrated in FIG. 16, the same components as those of the adjustment device 1a described with reference to FIG. 7 in the second embodiment are denoted by the same reference numerals, and redundant description will be omitted.

The adjustment device 1c is different from the adjustment device 1a according to the second embodiment in that a learning device 6 is mounted and a model storage unit 16 is provided. In addition, the specific operation of a determination unit 12c in the adjustment device 1c is different from the specific operation of the determination unit 12a in the adjustment device 1a according to the second embodiment.

The adjustment device 1c and the occupant state estimating device 2 constitute an adjustment system 100c.

In the "determination processing", the determination unit 12c determines whether or not it is necessary to check the state of the occupant on the basis of the estimation result collected by the estimated information collecting unit 11, the reference information collected by the reference information collecting unit 15, and the machine learning model. The reference information is vehicle interior environment determination information and abnormal-time motion determination information. The reference information may be either vehicle interior environment determination information or abnormal-time motion determination information.

In this case, the machine learning model is a machine learning model that uses the estimation result of the state of the occupant and the reference information as inputs and outputs the checking necessity information.

The machine learning model is generated by the learning device 6 and stored in the model storage unit 16.

The determination unit 12c acquires the machine learning model from the model storage unit 16, and performs "determination processing" on the basis of the estimation result collected by the estimated information collecting unit 11, the reference information collected by the reference information collecting unit 15, and the machine learning model. Specifically, the determination unit 12c obtains the checking necessity information output from the machine learning model using the estimation result collected by the estimated information collecting unit 11 and the reference information collected by the reference information collecting unit 15 as inputs of the machine learning model.

When obtaining the checking necessity information indicating that the checking is necessary, the determination unit 12c determines that it is necessary to check the state of the occupant. On the other hand, when obtaining the checking necessity information indicating that the checking is unnecessary, the determination unit 12c determines that it is not necessary to check the state of the occupant.

Note that, when the machine learning model is not stored in the model storage unit 16, the determination unit 12c determines whether or not it is necessary to check the state of the occupant by a method similar to that of the second embodiment, specifically, by determining whether or not there is an estimation result indicating an abnormal state continuously during the determination period among the estimation results indicating an abnormal state. The determination unit 12c shortens the determination period as necessary on the basis of the reference information.

In the adjustment device 1c in which the third embodiment is applied to the second embodiment, in the learning device 6, the learning data generating unit 61 generates the learning data including the estimation result of the state of the occupant, the reference information, and the checking necessity information.

In the adjustment device 1c, the estimated information collecting unit 11 stores the plurality of collected estimation results in the storage unit. In addition, the determination unit 12c stores, in the storage unit, the reference information collected by the reference information collecting unit 15 and the checking necessity information set on the basis of the result of whether or not it is determined that the state of the occupant needs to be checked when performing the "determination processing". The determination unit 12c stores the reference information and the checking necessity information in association with a plurality of corresponding estimation results, that is, a plurality of estimation results used in the "determination processing".

The learning data generating unit 61 acquires the estimation result of the state of the occupant collected by the estimated information collecting unit 11 from the occupant state estimating device 2, the reference information collected by the reference information collecting unit 15, and the checking necessity information set by the determination unit 12c, which are stored in the storage unit in association with each other, and generates learning data in which the acquired estimation result, the reference information, and the checking necessity information are associated with each other.

Note that the learning data generating unit 61 generates learning data when a preset number of associated estimation results, the reference information, and set occupant states are stored.

The learning data generating unit 61 outputs the generated learning data to the model generating unit 62.

The model generating unit 62 generates a machine learning model on the basis of the learning data generated by the learning data generating unit 61.

The model generating unit 62 causes a machine learning model configured by a neural network to learn by so-called supervised learning according to learning data generated on the basis of a combination of a plurality of estimation results, reference information, and checking necessity information.

The model generating unit 62 stores the generated machine learning model in the model storage unit 16.

The operation of the adjustment device 1c in the case of assuming that the machine learning model is generated is similar to the operation of the adjustment device 1b described with reference to FIG. 12 except for the specific operation of step ST2b.

In the adjustment device 1c, in step ST2b, the determination unit 12c performs "determination processing" on the basis of the plurality of estimation results collected by the estimated information collecting unit 11, the reference information collected by the reference information collecting unit 15, and the machine learning model.

Specifically, the determination unit 12c obtains checking necessity information output from the machine learning model using the estimation result collected by the estimated information collecting unit 11 and the reference information collected by the reference information collecting unit 15 as inputs of the machine learning model.

When obtaining the checking necessity information indicating that the checking is necessary, the determination unit 12c determines that it is necessary to check the state of the occupant. On the other hand, when obtaining the checking necessity information indicating that the checking is unnecessary, the determination unit 12c determines that it is not necessary to check the state of the occupant.

Note that, when the machine learning model is not generated, the adjustment device 1c performs the same operation as the operation of the adjustment device 1a described with reference to the flowchart of FIG. 8 in the second embodiment.

The operation of the learning device 6 mounted on the adjustment device 1c is similar to the operation of the learning device 6 described with reference to the flowchart of FIG. 14.

However, in step ST61, the learning data generating unit 61 generates learning data in which the estimation result, the reference information, and the checking necessity information are associated with each other.

Since the hardware configuration of the adjustment device 1c is similar to the hardware configuration of the adjustment device 1 according to the first embodiment described with reference to FIGS. 6A and 6B, illustration is omitted.

The functions of the estimated information collecting unit 11, the determination unit 12c, the state checking unit 13, the adjustment information output unit 14, and the reference information collecting unit 15 are implemented by the processing circuit 601. That is, the adjustment device 1c includes the processing circuit 601 for adjusting the method for estimating the state of the occupant in the occupant state estimating device 2 on the basis of the estimation result of the state of the occupant estimated by the occupant state estimating device 2.

The processing circuit 601 reads and executes the program stored in the memory 605, thereby executing the functions of the determination unit 12c, the state checking unit 13, the adjustment information output unit 14, and the reference information collecting unit 15. That is, the adjustment device 1c includes the memory 605 for storing a program that results in execution of steps ST1 to ST4 of FIG. 12 described above when executed by the processing circuit 601. In addition, it can also be said that the program stored in the memory 605 causes a computer to execute the procedures or methods performed the determination unit 12c, the state checking unit 13, the adjustment information output unit 14, and the reference information collecting unit 15.

In addition, the model storage unit 16 uses the memory 605. Note that this is an example, and the model storage unit 16 may be configured by an HDD, an SSD, a DVD, or the like.

The adjustment device 1c includes the input interface device 602 and the output interface device 603 that perform wired communication or wireless communication with a device such as the occupant state estimating device 2, the driving support device 3, the behavior determination information collecting device 4, or the reference information collecting device 5.

As described above, according to the third embodiment, the adjustment device 1b is configured to include: the estimated information collecting unit 11 to collect estimation results of the state of the occupant estimated by a plurality of the occupant state estimating devices 2; the determination unit 12b to determine whether or not it is necessary to check the state of the occupant on the basis of the estimation results collected by the estimated information collecting unit 11 and a machine learning model that outputs checking necessity information indicating whether or not it is necessary to check the state of the occupant using the estimation results as an input; the state checking unit 13 to determine a behavior of the occupant on the basis of behavior determination information for determining a behavior of the occupant and set the state of the occupant when the determination unit 12b determines that it is necessary to check the state of the occupant; and the adjustment information output unit 14 to output adjustment information for causing the occupant state estimating device 2 to adjust a state estimation condition used for estimating the state of the occupant so as to estimate the state of the occupant as the state of the occupant set by the state checking unit 13. Therefore, the adjustment device 1b can adjust the method for estimating the state of the occupant in the occupant state estimating device that estimates the state of the occupant. Further, the adjustment device 1b can adjust the method for estimating the state of the occupant in the occupant state estimating device 2 more quickly than the case of waiting for the determination period when determining whether or not to check the state of the occupant.

Further, as in the adjustment device 1c, the reference information collecting unit 15 to collect, as reference information, at least one of vehicle interior environment determination information for determining an environment in a vehicle and abnormal-time motion determination information for determining a motion that the occupant tends to perform in a case where the occupant is in an abnormal state may be provided, and the determination unit 12c may determine whether or not it is necessary to check the state of the occupant on the basis of the estimation results collected by the estimated information collecting unit 11, the reference information collected by the reference information collecting unit 15, and the machine learning model that uses the estimation results and the reference information as inputs and outputs the checking necessity information.

As a result, the adjustment device 1c can determine whether or not it is necessary to check the state of the occupant with higher accuracy as compared with the case of waiting for the determination period when determining whether or not to check the state of the occupant.

Note that, in the present disclosure, it is possible to freely combine each embodiment, to modify arbitrary components of each embodiment, or to omit arbitrary components in each embodiment.

INDUSTRIAL APPLICABILITY

An adjustment device according to the present disclosure can adjust a method for estimating a state of an occupant in an occupant state estimating device that estimates a state of an occupant.

REFERENCE SIGNS LIST

1, 1a, 1b, 1c: adjustment device, 11: estimated information collecting unit, 12, 12a, 12b, 12c: determination unit, 13: state checking unit, 131: behavior determination information collecting unit, 132: setting unit, 14: adjustment information output unit, reference information collecting unit, 16: model storage unit, 2: occupant state estimating device, 3: driving support device, 4: behavior determination information collecting device, 5: reference information collecting device, 51: in-vehicle environment information collecting device, 52: occupant motion information collecting device, 100, 100a, 100b, 100c: adjustment system, 6: learning device, 61: learning data generating unit, 62: model generating unit, 601, 1501: processing circuit, 602, 1502: input interface device, 603, 1503: output interface device, 604, 1504: CPU, 605, 1505: memory

The invention claimed is:

1. An adjustment device that adjusts an estimation method of a state of an occupant in at least one occupant state estimating device that includes a plurality of occupant state estimating devices and estimates the state of the occupant, the adjustment device comprising:
processing circuitry configured to:
collect estimation results of the state of the occupant estimated by the plurality of occupant state estimating devices;
determine whether or not it is necessary to check the state of the occupant on a basis of the collected estimation results and a machine learning model that outputs checking necessity information indicating whether or not it is necessary to check the state of the occupant using the estimation results as an input;
determine a behavior of the occupant on a basis of behavior determination information for determining the behavior of the occupant and set the state of the occupant when the processing circuitry determines that it is necessary to check the state of the occupant;
output adjustment information for causing the at least one occupant state estimating device to adjust a state estimation condition used for estimating the state of the occupant in such a manner that the state of the occupant is estimated as the state of the occupant having been set;

collect, as reference information, at least one of vehicle interior environment determination information for determining an environment in a vehicle and abnormal-time motion determination information for determining a motion that the occupant tends to make in a case where the occupant is in an abnormal state; and determine whether or not it is necessary to check the state of the occupant on a basis of the collected estimation results, the collected reference information, and the machine learning model that uses the estimation results and the reference information as inputs and outputs the checking necessity information.

2. The adjustment device according to claim 1, wherein the processing circuitry is further configured to generate learning data including the estimation results and the checking necessity information on a basis of the collected estimation results and a result of whether or not to check the determined state of the occupant; and generate the machine learning model on a basis of the generated learning data.

3. An adjustment system, comprising:

the adjustment device according to claim 1; and the at least one occupant state estimating device to adjust the state estimation condition used for estimating the state of the occupant on a basis of the output adjustment information.

4. An adjustment method that adjusts an estimation method of a state of an occupant in at least one occupant state estimating device that includes a plurality of occupant state estimating devices and estimates the state of the occupant, the adjustment method comprising:

collecting estimation results of the state of the occupant estimated by the plurality of occupant state estimating devices;

determining whether or not it is necessary to check the state of the occupant on a basis of the collected estimation results and a machine learning model that outputs checking necessity information indicating whether or not it is necessary to check the state of the occupant using the estimation results as an input;

determining a behavior of the occupant on a basis of behavior determination information for determining the behavior of the occupant and setting the state of the occupant when it is determined that it is necessary to check the state of the occupant;

outputting adjustment information for causing the at least one occupant state estimating device to adjust a state estimation condition used for estimating the state of the occupant in such a manner that the state of the occupant is estimated as the state of the occupant having been set;

collecting, as reference information, at least one of vehicle interior environment determination information for determining an environment in a vehicle and abnormal-time motion determination information for determining a motion that the occupant tends to make in a case where the occupant is in an abnormal state; and determining whether or not it is necessary to check the state of the occupant on a basis of the collected estimation results, the collected reference information, and the machine learning model that uses the estimation results and the reference information as inputs and outputs the checking necessity information.

\* \* \* \* \*